(12) United States Patent
Remmers et al.

(10) Patent No.: US 10,172,548 B2
(45) Date of Patent: Jan. 8, 2019

(54) SYSTEMS AND METHODS FOR PROVIDING AN AUTOMATED TITRATION FOR ORAL APPLIANCE THERAPY

(71) Applicant: ZST HOLDINGS, INC., Calgary (CA)

(72) Inventors: John Remmers, Sedona, AZ (US); Zbigniew Ludwik Topor, Calgary (CA); Joshua Grosse, Calgary (CA); Paul Cataford, Calgary (CA); Patrick Lecoz, Paris (FR)

(73) Assignee: ZST Holdings, Inc., Calgary (CA)

( * ) Notice: Subject to any disclaimer, the term of this patent is extended or adjusted under 35 U.S.C. 154(b) by 455 days.

(21) Appl. No.: 14/774,949

(22) PCT Filed: Mar. 10, 2014

(86) PCT No.: PCT/US2014/022638
§ 371 (c)(1),
(2) Date: Sep. 11, 2015

(87) PCT Pub. No.: WO2014/159236
PCT Pub. Date: Oct. 2, 2014

(65) Prior Publication Data
US 2016/0022205 A1  Jan. 28, 2016

Related U.S. Application Data

(60) Provisional application No. 61/783,241, filed on Mar. 14, 2013.

(51) Int. Cl.
*A61B 5/00* (2006.01)
*A61F 5/56* (2006.01)
(Continued)

(52) U.S. Cl.
CPC .......... *A61B 5/4836* (2013.01); *A61B 5/0871* (2013.01); *A61B 5/097* (2013.01);
(Continued)

(58) Field of Classification Search
CPC ..... A61B 5/4836; A61B 5/0871; A61B 5/097; A61B 5/4557; A61B 5/4818;
(Continued)

(56) References Cited

U.S. PATENT DOCUMENTS 2,171,695 A  9/1939  Harper
4,376,628 A  3/1983  Aardse
(Continued)

FOREIGN PATENT DOCUMENTS

CN  1602970  4/2005
CN  101917924  12/2010
(Continued)

OTHER PUBLICATIONS

International Preliminary Report on Patentability and Written Opinion, dated Sep. 24, 2015, received in connection with International Patent Application No. PCT/US2014/022638.
(Continued)

*Primary Examiner* — Ophelia A Hawthorne
(74) *Attorney, Agent, or Firm* — Meunier Carlin & Curfman LLC

(57) ABSTRACT

Provided herein are systems, methods and devices for performing one or more titrations for oral appliance therapy. For example, a method for evaluating an outcome of oral appliance therapy in a subject is discussed herein. The method can include positioning an adjustable mandibular displacement device in an oral cavity of a subject and implementing an automatic titration protocol. The protocol can include controlling a protrusion level of the adjustable mandibular displacement device during a test period, monitoring physiological information from the subject during the test period, and analyzing the physiological information to evaluate the outcome of oral appliance therapy.

44 Claims, 17 Drawing Sheets

(51) Int. Cl.
*A61B 5/087* (2006.01)
*A61B 5/097* (2006.01)
*A61B 5/145* (2006.01)
*A61B 7/00* (2006.01)
*A61M 16/00* (2006.01)
*A61M 16/04* (2006.01)

(52) U.S. Cl.
CPC ........ *A61B 5/14542* (2013.01); *A61B 5/4557* (2013.01); *A61B 5/486* (2013.01); *A61B 5/4818* (2013.01); *A61B 5/4848* (2013.01); *A61B 5/6819* (2013.01); *A61B 5/7246* (2013.01); *A61B 5/7264* (2013.01); *A61B 5/7275* (2013.01); *A61B 5/7282* (2013.01); *A61B 5/743* (2013.01); *A61B 7/003* (2013.01); *A61F 5/566* (2013.01); *A61M 16/0057* (2013.01); *A61M 16/0488* (2013.01); *A61B 2505/07* (2013.01); *A61B 2560/0475* (2013.01); *A61B 2562/0247* (2013.01); *A61F 2005/563* (2013.01)

(58) Field of Classification Search
CPC ..... A61B 5/4848; A61B 5/486; A61B 5/6819; A61B 5/7246; A61B 5/7264; A61B 5/7275; A61B 5/7282; A61B 5/743; A61B 7/003; A61F 5/566; A61F 5/56
See application file for complete search history.

(56) References Cited

U.S. PATENT DOCUMENTS

| | | | |
|---|---|---|---|
| 4,602,905 A | 7/1986 | O'Keefe | |
| 4,901,737 A | 2/1990 | Toone | |
| 5,030,098 A | 7/1991 | Branford | |
| 5,154,609 A | 10/1992 | George | |
| 5,313,960 A | 5/1994 | Tomasi | |
| 5,365,945 A | 11/1994 | Halstrom | |
| 5,409,017 A | 4/1995 | Lowe | |
| 5,427,117 A | 6/1995 | Thornton | |
| 5,513,986 A | 5/1996 | Feltham et al. | |
| 5,537,994 A | 7/1996 | Thornton | |
| 5,566,683 A | 10/1996 | Thornton | |
| 5,570,704 A | 11/1996 | Buzzard et al. | |
| 5,611,355 A | 3/1997 | Hilsen | |
| 5,642,737 A | 7/1997 | Parks | |
| 5,666,960 A | 9/1997 | Fredberg et al. | |
| 5,671,733 A | 9/1997 | Raviv et al. | |
| 5,678,567 A | 10/1997 | Thornton et al. | |
| 5,755,219 A | 5/1998 | Thornton | |
| 5,794,627 A | 8/1998 | Frantz et al. | |
| 5,816,799 A | 10/1998 | Parker | |
| 5,823,193 A | 10/1998 | Singer et al. | |
| 5,826,579 A | 10/1998 | Remmers et al. | |
| 5,829,441 A | 11/1998 | Kidd | |
| 5,846,212 A | 12/1998 | Beeuwkes et al. | |
| 5,868,138 A | 2/1999 | Halstrom | |
| 5,884,628 A | 3/1999 | Hilsen | |
| 5,921,942 A * | 7/1999 | Remmers ................ | A61F 5/566 600/529 |
| 5,941,247 A | 8/1999 | Keane | |
| 5,954,048 A | 9/1999 | Thornton | |
| 5,961,447 A | 10/1999 | Raviv et al. | |
| 5,983,892 A | 11/1999 | Thornton | |
| 6,012,920 A | 1/2000 | Woo | |
| 6,041,784 A | 3/2000 | Halstrom | |
| 6,055,986 A | 5/2000 | Meade | |
| 6,109,265 A | 8/2000 | Frantz et al. | |
| 6,155,262 A | 12/2000 | Thornton et al. | |
| 6,161,542 A | 12/2000 | Halstrom | |
| 6,273,859 B1 | 8/2001 | Remmers et al. | |
| 6,290,654 B1 | 9/2001 | Karakasoglu | |
| 6,305,376 B1 | 10/2001 | Thornton | |
| 6,325,064 B1 | 12/2001 | Thornton | |
| 6,374,824 B1 | 4/2002 | Thornton | |
| 6,450,167 B1 | 9/2002 | David et al. | |
| 6,516,805 B1 | 2/2003 | Thornton | |
| 6,634,353 B1 | 10/2003 | Knebelman et al. | |
| 6,729,335 B1 | 5/2004 | Halstrom | |
| 6,769,910 B1 | 8/2004 | Pantino | |
| 6,877,513 B2 | 4/2005 | Scarberry et al. | |
| 7,146,982 B2 | 12/2006 | Mousselon et al. | |
| 7,174,895 B2 | 2/2007 | Thornton et al. | |
| 7,282,027 B2 | 10/2007 | Sotos et al. | |
| 7,328,698 B2 | 2/2008 | Scarberry et al. | |
| 7,331,349 B2 | 2/2008 | Brady et al. | |
| 7,357,635 B2 | 4/2008 | Belfor et al. | |
| 7,396,333 B2 | 7/2008 | Stahmann et al. | |
| 7,328,705 B2 | 12/2008 | Abramson | |
| 7,637,262 B2 | 12/2009 | Bailey | |
| 7,712,468 B2 | 5/2010 | Hargadon | |
| 7,832,403 B2 | 11/2010 | Halstrom et al. | |
| 7,841,987 B2 | 11/2010 | Sotos et al. | |
| 8,001,973 B2 | 8/2011 | Sotos et al. | |
| 8,025,063 B2 | 9/2011 | Sotos et al. | |
| 8,037,886 B2 | 10/2011 | Sotos et al. | |
| 8,226,407 B2 | 7/2012 | Hanewinkel et al. | |
| 8,550,816 B2 | 10/2013 | Hanewinkel et al. | |
| 8,646,447 B2 | 2/2014 | Martin et al. | |
| 2002/0165462 A1 | 11/2002 | Westbrook et al. | |
| 2003/0224313 A1 | 12/2003 | Bergersen | |
| 2004/0030224 A1 | 2/2004 | Sotos et al. | |
| 2005/0028827 A1 | 2/2005 | Halstrom | |
| 2005/0081859 A1 | 4/2005 | Scarberry et al. | |
| 2005/0175709 A1 | 8/2005 | Baty et al. | |
| 2005/0175954 A1 | 8/2005 | Zacher | |
| 2005/0241646 A1 | 11/2005 | Sotos et al. | |
| 2006/0003292 A1 | 1/2006 | Lauren et al. | |
| 2006/0020178 A1 | 1/2006 | Sotos et al. | |
| 2006/0063981 A1 | 3/2006 | Sotos et al. | |
| 2006/0155205 A1 | 7/2006 | Sotos et al. | |
| 2006/0266356 A1 | 11/2006 | Sotos et al. | |
| 2007/0068534 A1 | 3/2007 | Bailey et al. | |
| 2007/0183572 A1 | 8/2007 | Drummond et al. | |
| 2007/0239056 A1 | 10/2007 | Moore | |
| 2007/0283967 A1 | 12/2007 | Bailey | |
| 2007/0283973 A1 | 12/2007 | Longley | |
| 2008/0053461 A1 | 3/2008 | Hirotsuka et al. | |
| 2008/0064008 A1 | 3/2008 | Schmitt | |
| 2008/0076094 A1 | 3/2008 | Hindin | |
| 2008/0236597 A1 | 10/2008 | Bergersen | |
| 2009/0078257 A1 | 3/2009 | Bhat et al. | |
| 2009/0078274 A1 | 3/2009 | Bhat et al. | |
| 2009/0241969 A1 | 10/2009 | Walker | |
| 2010/0018538 A1 * | 1/2010 | Sotos .................... | A61F 5/566 128/848 |
| 2010/0101583 A1 * | 4/2010 | Chen ................ | A61M 16/0051 128/207.14 |
| 2010/0154802 A1 | 6/2010 | Fuselier | |
| 2010/0163043 A1 | 7/2010 | Hart et al. | |
| 2010/0217426 A1 | 8/2010 | Sotos et al. | |
| 2010/0240982 A1 | 9/2010 | Westbrook et al. | |
| 2010/0300457 A1 | 12/2010 | Horchover | |
| 2010/0316973 A1 * | 12/2010 | Remmers ................ | A61F 5/566 433/214 |
| 2011/0005526 A1 | 1/2011 | Garabadian et al. | |
| 2011/0217674 A1 | 9/2011 | Hanewinkel et al. | |
| 2011/0232652 A1 * | 9/2011 | Levendowski ......... | A61F 5/566 128/848 |
| 2011/0295083 A1 | 12/2011 | Doelling et al. | |
| 2013/0023797 A1 | 1/2013 | Hanewinkel et al. | |
| 2014/0114146 A1 | 4/2014 | Hanewinkel et al. | |
| 2015/0007830 A1 | 1/2015 | Remmers et al. | |
| 2015/0039045 A1 | 2/2015 | Ni et al. | |
| 2015/0164682 A1 | 6/2015 | Remmers et al. | |

FOREIGN PATENT DOCUMENTS

| | | |
|---|---|---|
| CN | 102481181 | 5/2012 |
| EP | 1832306 | 9/2007 |
| JP | 2001-524852 | 12/2001 |
| WO | 1998/046177 | 10/1998 |

(56) References Cited

FOREIGN PATENT DOCUMENTS

| WO | 2005/107590 | 11/2005 |
|---|---|---|
| WO | 2005/115266 | 12/2005 |
| WO | 2008/151374 | 12/2008 |
| WO | 2010/141868 | 12/2010 |
| WO | 2010/141957 | 12/2010 |
| WO | 2011/082346 | 7/2011 |
| WO | 2011/147985 | 12/2011 |
| WO | 2013/102095 | 7/2013 |
| WO | 2013/188660 | 12/2013 |
| WO | 2014/170855 | 10/2014 |

OTHER PUBLICATIONS

Almeida, F.R., et al., "Effect of a Titration Polysomnogram on Treatment Success with a Mandibular Repositioning Appliance," Journal of Clinical Sleep Medicine, vol. 5, No. 3, 2009, pp. 198-204.

Cartwright, R.D., "Predicting Response to the Tongue Retaining Device for Sleep Apnea Syndrome," Arch. Otolaryngol., vol. 111, 1985, pp. 385-388.

Chan, A.S.L., et al., "Nasopharyngoscopic evaluation of oral appliance therapy for obstructive sleep apnoea," European Respiratory Journal, vol. 35, No. 4, 2010, pp. 836-842.

Clark, S.A., et al., "Assessment of Inspiratory Flow Limitation Invasively and Noninvasively during Sleep," American Journal of Respiratory and Critical Care Medicine, vol. 158, 1998, pp. 713-722.

Dort, L.C., et al., "Mandibular advancement and obstructive sleep apnoea: a method for determining effective mandibular protrusion," European Respiratory Journal, vol. 27, No. 5, 2006, pp. 1003-1009.

Friedman, M., et al., "Compliance and Efficacy of Titratable Thermoplastic versus Custom Mandibular Advancement Devices," Otolaryngology-Head and Neck Surgery, vol. 147, No. 2, 2012, pp. 379-386.

Kim, Y.-K., et al., "The influence of the amount of mandibular advancement in the application of mandibular advancement device for obstructive sleep apnea patients," Sleep Medicine and Psychophysiology, vol. 18, No. 6, 2011, pp. 29-34. (English Abstract).

Levendowski, D.J., et al., "Initial Evaluation of a Titration Appliance for Temporary Treatment of Obstructive Sleep Apnea," J. Sleep Disord. Ther., vol. 1, Issue 1, 2011, 8 pages.

Liu, Y., et al., "Cephalometric and physiologic predictors of the efficacy of an adjustable oral appliance for treating obstructive sleep apnea," American Journal of Orthodontics and Dentofacial Orthopedics, vol. 120, No. 6, 2001, pp. 639-647.

Marklund, M., et al., "Treatment Success With a Mandibular Advancement Device Is Related to Supine-Dependent Sleep Apnea," CHEST, vol. 114, No. 6, 1998, pp. 1630-1635.

Morgenstern, C., et al., "Assessment of Changes in Upper Airway Obstruction by Automatic Identification of Inspiratory Flow Limitation During Sleep," IEEE Transactions on Biomedical Engineering, vol. 56, No. 8, 2009, pp. 2006-2015.

Otsuka, R., et al., "A comparison of responders and nonresponders to oral appliance therapy for the treatment of obstructive sleep apnea," American Journal of Orthodontics and Dentofacial Orthopedics, vol. 129, No. 2, 2006, pp. 222-229.

Pételle, B., et al., "One-Night Mandibular Advancement Titration for Obstructive Sleep Apnea Syndrome," American Journal of Respiratory and Critical Care Medicine, vol. 165, 2002, pp. 1150-1153.

Remmers, J., et al., "Remotely Controlled Mandibular Protrusion during Sleep Predicts Therapeutic Success with Oral Appliances in Patients with Obstructive Sleep Apnea," Sleep, vol. 36, No. 10, 2013, pp. 1517-1525A.

Tsai, W.H., et al., "Remotely Controlled Mandibular Positioner Predicts Efficacy of Oral Appliances in Sleep Apnea," American Journal of Respiratory and Critical Care Medicine, vol. 170, No. 4, 2004, pp. 366-370.

Tsuiki, S., et al., "Optimal positive airway pressure predicts oral appliance response to sleep apnoea," European Respiratory Journal, vol. 35, No. 5, 2010, pp. 1098-1105.

Vázquez, J.-C., et al., "Automated analysis of digital oximetry in the diagnosis of obstructive sleep apnoea," Thorax., vol. 55, 2000, pp. 302-307.

International Search Report and Written Opinion of the International Searching Authority from the International Application No. PCT/US2014/022638 dated Feb. 6, 2015.

Supplemenatry Search Report issued in European Application No. 14776224.7, dated Oct. 7, 2016.

Communication Pursuant to Article 94(3) EPC, issued in European Application No. 14776224.7, dated Oct. 26, 2016.

Communication Pursuant to Article 94(3) EPC, issued in European Application No. 14776224.7, dated Aug. 29, 2017.

Office Action issued in Chinese Application No. 201480013459.3, dated Jun. 14, 2018 (with English-language translation).

Office Action issued in Chinese Application No. 201480013459.3, dated Nov. 3, 2017(with English-language translation).

Office Action issued in Chinese Application No. 201480013459.3, dated Dec. 30, 2016(with English-language translation).

International Preliminary Report on Patentability issued in International Application No. PCT/IB2016/051857, dated Oct. 12, 2017.

Office Action issued in Japanese Application No. 2016-501023, dated Apr. 2, 2018(with English-language translation).

Examination report issued in Australian Application No. 2014241067, dated Apr. 9, 2018.

De Backer, et al., "Functional imaging using computational fluid dynamics to predict treatment success of mandibular advancement devices in sleep-disordered breathing", Journal of Biomechanics, 2007, vol. 40, pp. 3708-3714.

* cited by examiner

SYSTEMS AND METHODS FOR PROVIDING AN AUTOMATED TITRATION FOR ORAL APPLIANCE THERAPY

CROSS-REFERENCE TO RELATED APPLICATIONS

This application claims the benefit of U.S. Provisional Patent Application No. 61/783,241, filed on Mar. 14, 2013, entitled "SYSTEMS AND METHODS FOR PROVIDING AN AUTOMATED TITRATION FOR ORAL APPLIANCE THERAPY," the disclosure of which is expressly incorporated herein by reference in its entirety.

BACKGROUND

Obstructive sleep apnea (OSA) is a common disease that is largely under-diagnosed and untreated. Nasal continuous positive airway pressure (CPAP) is the standard treatment for OSA. CPAP entails use of a nose mask to deliver positive pressure, which dilates a subject's pharynx and eliminates obstruction. This therapy is highly efficacious and benign but is associated with low adherence in many subjects, particularly those with disease of mild and moderate severity. The principal alternative to CPAP therapy is oral appliance (OA) therapy in which a custom made mandibular repositioner (MR) is used to protrude the subject's mandible during sleep, thereby opening the subject's pharyngeal airway. OA therapy, while preferred and well accepted by most subjects, is not uniformly effective in eliminating sleep apnea.

The effectiveness of OA therapy can be improved by screening OSA subjects and prospectively identifying those suitable for this therapy. Studies of the passive pharynx indicate that the response of the pharynx to mandibular protrusion is dose dependent. In other words, incremental mandibular protrusion produces corresponding pharyngeal enlargement. However, clinical experience shows that excessive mandibular protrusion is undesirable, producing side effects, such as, pain and tooth movement that lead to discontinuation of therapy. In some cases, over-protrusion can worsen OSA. According to current practice, a treatment provider such as a dentist progressively protrudes the subject's mandible until a symptomatic response occurs. The subject is then reassessed to determine if OSA has resolved.

Prospective identification of suitable candidates, as well as target effective protrusion levels, can greatly facilitate treatment of OSA with OA therapy. U.S. Pat. No. 5,826,579 to Remmers et al., entitled "Remote-Controlled Mandibular Positioning Device and Method of Using the Device," which is incorporated herein in its entirety by reference, describes a remotely-controlled mandibular positioner (RCMP). Additionally, U.S. Pat. No. 6,273,859 to Remmers et al., entitled "Adaptively Controlled Mandibular Positioning Device and Method of Using the Device," which is incorporated herein in its entirety by reference, describes an OA therapy which is an automatically-controlled mandibular positioner (ACMP).

Conventionally, the overall approach to the titration for OA therapy is to evaluate the physiological response (e.g., respiratory events such as apneas, hypopneas, snoring etc. and/or evidence of obstructions) at discrete levels mandibular protrusion. For example, the level of protrusion is maintained constant all night and therapeutic effectiveness can be assessed offline at the end of the night (e.g., using conventional home monitors). Alternatively, therapeutic effectiveness is assessed offline by evaluating the physiologic response at various levels of protrusion that are collected during a polysomnographic study during which a technician either manually (e.g., at the MR) or remotely (e.g., using the RCMP) adjusts an MR. In addition, when providing OA therapy, the level of protrusion can be held at the level of protrusion determined to be therapeutically effective, or it can be automatically adjusted in response to evidence of obstruction (e.g., using the ACMP).

SUMMARY

Provided herein are systems, methods and devices for performing one or more titrations for oral appliance therapy. For example, a method for evaluating an outcome of oral appliance therapy in a subject is discussed herein. The method can include positioning an adjustable mandibular displacement device in an oral cavity of a subject and implementing an automatic titration protocol. The protocol can include controlling a protrusion level of the adjustable mandibular displacement device during a test period, monitoring physiological information from the subject during the test period, and analyzing the physiological information to evaluate the outcome of oral appliance therapy.

The evaluation can optionally include predicting whether the subject is a favorable candidate for oral appliance therapy. Alternatively or additionally, the evaluation can optionally include predicting an effective protrusion level of the adjustable mandibular displacement device. Alternatively or additionally, the evaluation can optionally include predicting an optimal effective protrusion level of the adjustable mandibular displacement device.

The method can optionally further include controlling a protrusion level of the adjustable mandibular displacement device during the test period based on the monitored physiological information. For example, analyzing or monitoring the physiological information can include detecting one or more respiratory events. Detecting one or more respiratory events can include calculating a difference between the physiological information and a reference value and comparing the calculated difference to a threshold value. The reference value can be at least one of a baseline value or a real-time value for the physiological information. In addition, in the absence of respiratory events (i.e., during steady state breathing) the protrusion level can be controlled to induce changes in physiological information that can be used to further optimize the protrusive level.

For example, the physiological information can include respiratory airflow and oxygen saturation. The physiological information can also include other information related to a subject including, but not limited to, acoustic energy or vibration generated by the subject, sleep position or sleep stage, force on the subject's teeth, including combinations thereof.

The method can also include determining a frequency of occurrence of the one or more respiratory events. If the frequency of occurrence of the one or more respiratory events is greater than a predetermined threshold, the method can further include increasing the protrusion level of the adjustable mandibular displacement device. For example, the protrusion level can be increased until the frequency of occurrence of the one or more respiratory events is less than the predetermined threshold. Alternatively or additionally, if the frequency of occurrence of the one or more respiratory events is less than a predetermined threshold, the method can further include controlling a protrusion level of the adjustable mandibular displacement device to optimize at least one physiological input, for instance respiratory airflow.

A method for performing a titration for oral appliance therapy using a comprehensive data set is also discussed herein. For example, the method can include positioning an adjustable mandibular displacement device in an oral cavity of a subject during a test period, monitoring physiological information from the subject during the test period, controlling a protrusion level of the adjustable mandibular displacement device during the test period, and evaluating an outcome of oral appliance therapy based on a history of movement of the adjustable mandibular displacement device and the physiological information during the test period.

For example, evaluating an outcome of oral appliance therapy can include predicting whether the subject is a favorable candidate for oral appliance therapy. Alternatively or additionally, evaluating an outcome of oral appliance therapy can include identifying an effective protrusion level of the adjustable mandibular displacement device. An effective protrusion level of the adjustable mandibular displacement device can be a protrusion level that reduces the severity or frequency of respiratory events below an acceptable level. Alternatively or additionally, evaluating an outcome of oral appliance therapy can include identifying an optimal effective protrusion level of the adjustable mandibular displacement device.

The monitored physiological information can include, but is not limited to, respiratory airflow, oxygen saturation, sleep stage, sleep position, acoustic energy or vibration generated by the subject or force applied to a subject's teeth, including combinations thereof. For example, in some implementations, monitoring physiological information from the subject can include receiving one or more physiological inputs from the subject during the test period, and detecting one or more respiratory events during the test period using the one or more physiological inputs. The one or more respiratory events discussed herein can be an apnea, a hypopnea, a flow limited breath, a snoring event, etc. Alternatively or additionally, a respiratory event can be any event that is defined and measured according to predetermined criteria.

In addition, the method can include monitoring changes in a protrusion level of the adjustable mandibular displacement device during the test period. For example, the changes in the protrusion level of the adjustable mandibular displacement device can define the history of movement of the adjustable mandibular displacement device. Optionally, the history of movement of the adjustable mandibular displacement device can include movement between at least two protrusion levels. Additionally, the history of movement can include an amount of time the adjustable mandibular displacement device spends at each of the at least two protrusion levels.

Optionally, the method can include analyzing the history of movement to determine a percentage of time the adjustable mandibular displacement device spends at or below (i.e., at or less than) each of the at least two protrusion levels. In addition, evaluating an outcome of oral appliance therapy can optionally be performed based on a frequency of respiratory events at or above (i.e., at or greater than) each of the at least two protrusion levels. In addition, evaluating an outcome of oral appliance therapy can be performed based on both a frequency of respiratory events at or above each of the at least two protrusion levels and the percentage of time the adjustable mandibular displacement device spends at or below each of the at least two protrusion levels. In some implementations, the method can include generating a graphical representation that displays the frequency of respiratory events at or above each of the at least two protrusion levels, for example. Alternatively or additionally, the graphical representation can display the percentage of time the adjustable mandibular displacement device spends at or below each of the at least two protrusion levels. Evaluating an outcome of oral appliance therapy can optionally be performed based on the graphical representation. For example, a determination of whether a subject is a favorable candidate for oral appliance therapy and/or an effective protrusion level can be made using the graphical representation.

In some implementations, a protrusion level of the adjustable mandibular displacement device can be automatically controlled during the test period. For example, the adjustable mandibular displacement device can be a remote-controlled mandibular displacement device. As discussed below, a remote-controlled mandibular displacement device can be adjusted without having a technician manually adjust the mandibular displacement device locally (e.g., at or adjacent to the subject's oral cavity). In the case of automatically controlled, the remote-controlled mandibular displacement device can be adjusted without action from a technician, either locally or remotely. Optionally, the technician can be completely absent such as when the titration is performed in a non-clinical setting, for example, in the subject's home. Optionally, the technician can be present and optionally observing the subject, either remotely or locally, during the titration while the remote-controlled mandibular displacement device is adjusted without action from the technician.

In some implementations, evaluating an outcome of oral appliance therapy can include determining whether a frequency of respiratory events at or above a given protrusion level during the test period is less than a predefined value. Alternatively or additionally, evaluating an outcome of oral appliance therapy can include determining whether a percentage of time at or below the given protrusion level is greater than or equal to a predefined percentage of the test period. Optionally, the method can include determining that an effective protrusion level for oral appliance therapy is a smallest protrusion level where the frequency of respiratory events at or above the given protrusion level during the test period is less than the predefined value and the percentage of time at or below the given protrusion level is greater than or equal to the predefined percentage of the test period.

The method can optionally include calculating a frequency of respiratory events at a plurality of protrusion levels. For example, a number of respiratory events at or above each of the plurality of protrusion levels can be determined. Each of the number of respiratory events can then be divided by an amount of time the adjustable mandibular displacement device spends at or above each of the plurality of protrusion levels. The frequency of respiratory events can optionally be calculated at a plurality of protrusion levels where an amount of time the adjustable mandibular displacement device spends at or above each of the plurality of protrusion levels is at least 5 minutes. Optionally, evaluating an outcome of oral appliance therapy can include identifying one or more of the plurality of protrusion levels where the frequency of respiratory events is less than the predefined value. For example, the predefined value can be an acceptable number of events per hour such as 10 events per hour. Additionally, evaluating an outcome of oral appliance therapy can include determining whether a percentage of time at or below each of the one or more protrusion levels is greater than or equal to a predefined percentage of the test period. For example, the predefined percentage of the test period can be between 75% and 100% such as 85% of the test period. Similarly to above, the method can include determining that an effective protrusion level for oral appliance therapy is a smallest protrusion level where the frequency of respiratory events at the one or more of the plurality of protrusion levels during the test period is less than the predefined value and the percentage of time at or below the one or more of the plurality of protrusion levels is greater than or equal to the predefined percentage of the test period.

In some implementations, evaluating an outcome of oral appliance therapy can include indicating an optimal effective protrusion level of the adjustable mandibular displacement device using the one or more physiological inputs from the subject.

The test period can be while the subject is sleeping. For example, the test period can be a single sleep session. Optionally, the test period can include multiple sleep sessions. Alternatively or additionally, the test period and/or one or more of the sleep sessions can be at least 5 hours. The test period can optionally have a duration less than one night or can optionally have a duration of an entire night.

Additionally, controlling a protrusion level of the adjustable mandibular displacement device during the test period can include at least one of increasing protrusion level or decreasing protrusion level of the adjustable mandibular displacement device. Alternatively or additionally, controlling a protrusion level of the adjustable mandibular displacement device during the test period can include adjusting the protrusion level of the adjustable mandibular displacement device based on at least one of frequency or severity of the one or more respiratory events. At least one of a magnitude or rate of adjustment (e.g., either a magnitude or rate of adjustment) can optionally be related to at least one of the frequency or the severity of the one or more respiratory events. Alternatively or additionally, both the magnitude and rate of adjustment can optionally be related to at least one of the frequency or the severity of the one or more respiratory events. For example, a greater magnitude and/or rate of adjustment of the protrusion level of the adjustable mandibular displacement device can correspond to a more frequent or severe respiratory event, and a lesser magnitude and/or rate of adjustment of the protrusion level of the adjustable mandibular displacement device can correspond to a less frequent or severe respiratory event.

Optionally, monitoring physiological information from the subject during the test period can include classifying a magnitude of severity of at least one of the one or more respiratory events. At least one of a magnitude and a rate of adjustment of the protrusion level of the adjustable mandibular displacement device can be controlled based on the magnitude of severity of the respiratory event.

For example, when the one or more physiological inputs from the subject include oxygen saturation and respiratory airflow, classifying a magnitude of severity of a respiratory event can include classifying a severity level of a decrease in oxygen saturation associated with the respiratory event into one of n categories, and classifying a severity level of a decrease in respiratory airflow associated with the respiratory event into one of m categories. The magnitude of the severity of the respiratory event can be determined using an n×m matrix based on the severity levels of the decrease in oxygen saturation and the decrease in respiratory airflow associated with the respiratory event, where n and m are integers>1. At least one of a magnitude and a rate of adjustment of the protrusion level can be controlled based on the magnitude of the severity determined using the n×m matrix.

For example, m can be 3, and a first category can correspond to an approximately 80-100% decrease in respiratory airflow, a second category can correspond to an approximately 45-79% decrease in respiratory airflow, and a third category can correspond to an approximately 30-44% decrease in respiratory airflow. Alternatively or additionally, n can be 3, and a first category can correspond to at least an approximately 6% decrease in oxygen saturation from real-time or baseline oxygen saturation, a second category can correspond to between an approximately 3% and 6% decrease in oxygen saturation from real-time or baseline oxygen saturation and a third category can correspond to a less than an approximately 3% decrease in oxygen saturation from real-time or baseline oxygen saturation.

Optionally, monitoring physiological information from the subject during the test period can further include classifying a frequency level of at least one of the one or more respiratory events. At least one of a magnitude and a rate of adjustment of the protrusion level can be controlled based on the frequency level of the respiratory event. For example, a magnitude of the severity of the respiratory event can be determined as discussed above (e.g., using the n×m matrix). Optionally, a frequency at which the respiratory event occurs is calculated. The frequency at which the respiratory event occurs can be multiplied by the magnitude of the severity level of the respiratory event to obtain a frequency-severity index.

The protrusion level of the adjustable mandibular displacement device can be controlled during the test period based on the frequency-severity index. Optionally, the frequency of respiratory events having substantially the same magnitude of severity are determined and then multiplied by the magnitude of severity to obtain a frequency-severity index. A global frequency-severity index can be calculated by summing the frequency-severity indexes for a plurality of respiratory events. The protrusion level of the adjustable mandibular displacement device can be controlled during the test period based on the global frequency-severity index.

Alternatively or additionally, a frequency level of the respiratory event can be classified into one of q categories and a frequency-severity index can be obtained using an n×m×q matrix based on the severity and frequency levels associated with the respiratory event, where n and m and q are integers>1. The protrusion level of the adjustable mandibular displacement device can be controlled during the test period based on the frequency-severity index.

Optionally, a protrusion level of the adjustable mandibular displacement device during the test period can also be controlled in response to not detecting a respiratory event during a fixed period of time during the test period. For example, the protrusion level can be adjusted to induce a change in respiratory airflow. For example, a predefined adjustment can be used to induce a change in respiratory airflow. Alternatively or additionally, at least one of a magnitude and rate of adjustment of the protrusion level can be determined using a matrix of one of the classifications of severity, either severity of oxygen desaturation or severity of decrease in airflow, along with a measure of frequency or any of these measures on their own.

Alternatively or additionally, a protrusion level of the adjustable mandibular displacement device during the test period can be controlled in response to a frequency of respiratory events falling below a predetermined threshold by adjusting protrusion level of the adjustable mandibular displacement device to optimize respiratory airflow. For example, a first protrusion level beyond which a decrease in the protrusion level results in a decrease respiratory airflow can be identified. Additionally, a second protrusion level beyond which an increase in the protrusion level does not result in an increase in respiratory airflow can also be identified. Optionally, an effective protrusion level for oral appliance therapy can be approximately between the first protrusion level and the second protrusion level. Alternatively or additionally, a third protrusion level where a small increase in the protrusion level results in an insignificant change in respiratory airflow and a small decrease in the protrusion level results in a signification change in respiratory airflow can be identified. Optionally, an effective protrusion level for oral appliance therapy can be approximately the third protrusion level.

In some implementations, the method can include detecting one or more respiratory events by detecting a decrease in oxygen saturation within a period of time after detecting a decrease in respiratory airflow. Optionally, the period of time can be subject-specific and determined based on an analysis of the detected respiratory events. Optionally, the period of time can be fixed, such as approximately 10-40 seconds, for example. The analysis can be performed before the test period. Alternatively or additionally, the analysis can be performed during the test period.

An example method for performing a titration for oral appliance therapy can be performed based on data collected at a plurality of protrusion levels of an adjustable mandibular displacement device is also discussed herein. For example, the method can include receiving physiological data collected from a subject during a test period, receiving data related to a protrusion level of the adjustable mandibular displacement device during the test period and evaluating an outcome of oral appliance therapy based on the physiological data collected from the subject at the plurality of protrusion levels of the adjustable mandibular displacement device during the test period.

An example method for performing a titration for oral appliance therapy in a non-clinical setting is also discussed herein. The method can include positioning an adjustable mandibular displacement device in an oral cavity of a subject during a test period, controlling a protrusion level of the adjustable mandibular displacement device during the test period, collecting one or more physiological inputs from the subject during the test period and analyzing the one or more physiological inputs collected from the subject and a history of movement of the adjustable mandibular displacement device during the test period. Additionally, the protrusion level can be controlled by moving the adjustable mandibular displacement device between at least two protrusion levels.

The method can further include evaluating an outcome of oral appliance therapy. Similarly to the methods discussed herein, a determination as to whether the subject is a favorable candidate for oral appliance therapy and/or an effective protrusion level of the adjustable mandibular displacement device can be determined by analyzing the one or more physiological inputs collected from the subject and a history of movement of the adjustable mandibular displacement device during the test period.

The non-clinical setting can be a sleep session occurring outside of a sleep clinic. For example, the non-clinical setting can be a sleep session occurring in the subject's home. Alternatively or additionally, the non-clinical setting can be a sleep session occurring without a polysomnographic technician monitoring the subject and/or without conducting a polysomnographic study. Optionally, the favorable candidate can be identified regardless of knowledge of the complete information that would be obtained under polysomnographic monitoring, for instance without knowledge of a sleep stage during the test period, a body position during the test period or of other inputs that would support the identification of a period in which the patient is experiencing a worst case scenario of obstruction.

The test period can be while the subject is sleeping. For example, the test period can be a single sleep session. Optionally, the test period can include multiple sleep sessions. Alternatively or additionally, the test period and/or one or more of the sleep sessions can be at least 5 hours. The test period can optionally have a duration less than one night or can optionally have a duration of an entire night. A titration can optionally include multiple test periods, which can be averaged or combined in some way to complete the titration.

In the non-clinical setting, the monitored physiological information can include respiratory airflow and oxygen saturation. Optionally, in the non-clinical setting, the monitored physiological information can only include respiratory airflow and oxygen saturation. Accordingly, the physiological inputs can include respiratory airflow and oxygen saturation and exclude information collected during a polysomnographic study, for example. As discussed above, the favorable candidate can be identified regardless of knowledge of the complete information that would be obtained under polysomnographic monitoring. Respiratory airflow and oxygen saturation can be received from the subject during the test period, and one or more respiratory events can be detected during the test period using the received respiratory airflow and oxygen saturation. The one or more respiratory events discussed herein can be an apnea, a hypopnea, a flow limited breath, a snoring event, etc. Alternatively or additionally, a respiratory event can be any event that is defined and measured according to predetermined criteria.

In some implementations, the method can include detecting one or more respiratory events by detecting a decrease in oxygen saturation and a decrease in respiratory airflow within a period of time. Optionally, detecting one or more respiratory events includes detecting a decrease in oxygen saturation within a period of time after detecting a decrease in respiratory airflow. Optionally, the period of time can be subject-specific and determined based on an analysis of the detected oxygen and airflow events. The analysis can optionally be performed before the test period. For example, the analysis can be performed using data from a data collection period prior to the test period. Alternatively or additionally, the analysis can optionally be performed during the test period. Optionally, a first test period within the test period with a fixed, standard time lag can be used. For example, the first test period within the test period can be fixed and approximately 10-40 seconds. The data from the first test period can be used to determine a subject-specific time lag that is then used in subsequent periods within the test period for detecting respiratory events as discussed above.

Additionally, the method can include classifying a severity level of the respiratory event. Alternatively or additionally, the method can include classifying a frequency level of the respiratory event. At least one of a magnitude and a rate of adjustment of the protrusion level can be adjusted based on the severity and/or frequency level of the respiratory event. For example, a greater magnitude and/or rate of adjustment of the protrusion level of the adjustable mandibular displacement device can correspond to a more frequent or severe respiratory event, and a lesser magnitude and/or rate of adjustment of the protrusion level of the adjustable mandibular displacement device can correspond to a less frequent or severe respiratory event.

Predicting whether the subject is a favorable candidate for oral appliance therapy can further include determining a frequency of respiratory events at or above each protrusion level during the test period. Alternatively or additionally, predicting whether the subject is a favorable candidate for oral appliance therapy can further include determining a percentage of time at or below each protrusion level during the test period. The candidate can be favorable when the frequency of respiratory events is less than a predefined value or the percentage of time is greater than a predefined percentage of the test period. Optionally, the candidate can be favorable when the frequency of respiratory events is less than the predefined value and the percentage of time is greater than the predefined percentage. Additionally, an effective protrusion level for oral appliance therapy can be a smallest protrusion level where the frequency of respiratory events is less than the predefined value and the percentage of time is greater than or equal to the predefined percentage.

An example method for automatically controlling an adjustable mandibular displacement device while performing a titration for oral appliance therapy is also discussed herein. The method can include monitoring physiological information from a subject during a test period, where the test period includes at least one event period and at least one non-event period. The method can also include analyzing the monitored physiological information to determine if the subject is in the at least one event period or the at least one non-event period, controlling a protrusion level of the adjustable mandibular displacement device during the at least one event period, controlling the protrusion level of the adjustable mandibular displacement device during the at least one non-event period, and collecting data during the at least one event period and the at least one non-event period.

An event period includes a portion of the test period where a frequency of the one or more respiratory events is greater than a predetermined threshold. Additionally, a non-event period includes a portion of the test period wherein a frequency of the one or more respiratory events is less than a predetermined threshold. In some implementations, collecting data can include collecting data regarding a history of movement of the adjustable mandibular displacement device during the at least one event period and the at least one non-event period. Alternatively or additionally, analyzing the monitored physiological information can include detecting one or more respiratory events.

Controlling a protrusion level of the adjustable mandibular displacement device during the at least one event period can include at least one of increasing the protrusion level or decreasing the protrusion level of the adjustable mandibular displacement device. Optionally, controlling a protrusion level of the adjustable mandibular displacement device during the at least one event period can include adjusting the protrusion level of the adjustable mandibular displacement device based on at least one of frequency or severity of the one or more respiratory events. As discussed above, at least one of a magnitude and rate of adjustment can be related to at least one of the frequency or the severity of the one or more respiratory events.

Additionally, a severity level of the respiratory event can be classified, for example, into a plurality of categories as discussed above. Alternatively or additionally, a frequency level of the respiratory event can be classified, for example, into a plurality of categories as discussed above. At least one of a magnitude and a rate of adjustment of the protrusion level can be adjusted based on the severity and/or frequency level of the respiratory event. For example, a greater magnitude and/or rate of adjustment of the protrusion level of the adjustable mandibular displacement device can correspond to a more frequent or severe respiratory event, and a lesser magnitude and/or rate of adjustment of the protrusion level of the adjustable mandibular displacement device can correspond to a less frequent or severe respiratory event.

In addition, controlling the protrusion level of the adjustable mandibular displacement device during the at least one non-event period can include adjusting the protrusion level to induce a change in at least one physiological input such as respiratory airflow. For example, the protrusion level of the adjustable mandibular displacement device can be controlled to optimize respiratory airflow.

For example, a first protrusion level beyond which a decrease in the protrusion level results in a decrease respiratory airflow can be identified. Additionally, a second protrusion level beyond which an increase in the protrusion level does not result in an increase in respiratory airflow can also be identified. Alternatively or additionally, a third protrusion level where a small increase in the protrusion level results in an insignificant change in respiratory airflow and a small decrease in the protrusion level results in a signification change in respiratory airflow can be identified.

An example method for detecting respiratory events is discussed herein. An example method for detecting respiratory events can include receiving at least one physiological input (e.g., oxygen saturation) from a subject, detecting at least one oxygen saturation event based on the received physiological input and classifying the oxygen saturation event as a respiratory event if a decrease in oxygen saturation of at least a predefined amount from baseline oxygen saturation is detected. For example, the predefined amount can be approximately 6%.

Alternatively or additionally, the method can include receiving one or more physiological inputs (e.g., respiratory airflow and oxygen saturation, for example) from a subject, detecting at least one oxygen saturation event based on the received physiological input, detecting at least one respiratory airflow event based on the received physiological inputs, matching the oxygen saturation event and the respiratory airflow event and classifying the matched oxygen saturation event and respiratory airflow event as a respiratory event if the oxygen saturation event and the respiratory airflow event are detected within a period of time. For example, the matched oxygen saturation event and respiratory airflow event can be classified as a respiratory event when the oxygen saturation event occurs within a predetermined time after the respiratory airflow event.

The matched oxygen saturation event and respiratory airflow event can be classified as a respiratory event in real-time during a test period. For example, the oxygen saturation event and respiratory airflow event can be matched while continuing to receive one or more physiological inputs from the subject. After matching the oxygen saturation event and respiratory airflow event, a respiratory event can be classified, which also occurs in real-time. For example, the oxygen saturation and respiratory airflow event can optionally be matched by their occurrence with a period of time from one another. The period of time can be a fixed, standard period of time applied to all subjects (e.g., 10-40 seconds). Alternatively, the period of time can optionally be subject-specific and can be determined based on an analysis of the one or more physiological inputs from the subject. The analysis to determine the subject-specific period of time can be performed before conducting a titration for oral appliance therapy on the subject. Alternatively or additionally, the analysis can be performed while conducting a titration for oral appliance therapy on the subject. For example, the analysis to identify the period of time can be conducted during a first period of time within the titration.

In some implementations, detecting an oxygen saturation event can include detecting a decrease in oxygen saturation of at least a minimum amount from baseline oxygen saturation. For example, the minimum amount can be 1.5%. Optionally, the method can include calculating the baseline oxygen saturation as a moving average. Calculating the moving average can include receiving a plurality of oxygen saturation samples during a moving average time period, and averaging one or more of the plurality of oxygen saturation samples having oxygen saturation within in an Xth percentile among the plurality of oxygen saturation samples. For example, one or more of the plurality of oxygen saturation samples having oxygen saturation within the top $25^{th}$ percentile among all of the oxygen saturation samples can be included in the average. Detecting oxygen saturation events as decreases of a minimum amount from a baseline can provide an accurate way of calculating a severity level of the decrease in oxygen saturation.

Alternatively or additionally, detecting an oxygen saturation event can include detecting a decrease in the real-time value of oxygen saturation of at least a minimum amount. In other words, a decrease that is not calculated from baseline oxygen saturation can be used. For example, the minimum amount can be 1.5%. Alternatively or additionally, detecting an oxygen saturation event can include detecting a plurality of consecutive decreases in oxygen saturation followed by an increase in oxygen saturation. For example, the plurality of consecutive decreases in oxygen saturation can include at least 3 consecutive decreases. Optionally, the consecutive decreases in oxygen saturation can be of a certain threshold. For example, three consecutive decreases of at least 0.5%. Detecting oxygen saturation events as decreases from a real-time value (as opposed to a baseline value) can prevent missing an oxygen saturation event when recovering from a previous oxygen saturation event.

Additionally, detecting a respiratory airflow event can include detecting a monotonic decrease followed by an increase in respiratory airflow from a reference respiratory airflow. Optionally, reference respiratory airflow can represent an average breath and/or average respiratory airflow while the subject is sleeping. A change from reference respiratory airflow can be used to identify respiratory events. For example, a reference respiratory airflow can optionally be calculated as a moving average. For example, reference respiratory airflow can be calculated during a moving average time period (e.g., 10 seconds).

Optionally, the respiratory airflow is measured as a breath-by-breath minute ventilation. Detecting a respiratory airflow event can include detecting a change in breath-by-breath minute ventilation from a reference breath-by-breath minute ventilation. Minute ventilation is the volume of inhaled air expressed in liters per minute (L/min), and the breath-by-breath minute ventilation is the volume of air inhaled within an individual breath. Calculating the breath-by-breath minute ventilation requires detection of the limits of inspiration for each breath. Determination of the limits of inspiration requires detection of a baseline respiratory airflow value on which to identify the onset and end of inspiration. For example, the baseline respiratory airflow can be calculated as a moving average. Calculating the moving average can include receiving a plurality of respiratory airflow samples during a moving average time period, and calculating the moving average as a moving mode based on the plurality of respiratory airflow samples. For instance, the airflow signal could be sampled at 25 Hz and the width of the window could be 20 minutes when calculating baseline respiratory airflow. Alternatively or additionally, calculating the moving average can include receiving a plurality of respiratory airflow samples during a moving average time period, and calculating the moving average as a moving median based on the plurality of respiratory airflow samples. For instance, the airflow signal could be sampled at 25 Hz and the width of the window could be 20 minutes when calculating baseline respiratory airflow. These calculation methods are suited for real time detection of a baseline respiratory airflow. Alternatively or additionally, these calculation methods can be used in an offline analysis.

Detecting a respiratory airflow event can include detecting changes in breath-by-breath minute ventilation. These changes may be calculated with respect to a reference breath-by-breath minute ventilation. The reference breath-by-breath minute ventilation can be the average breath-by-breath minute ventilation over a plurality of breaths. The breath-by-breath minute ventilation can be calculated on the basis of an individual inspiration. Optionally, the method can include calculating the breath-by-breath as a moving average. For example, the width of the window could be 10 seconds. Alternatively or additionally, detecting respiratory airflow events can include detecting changes in peak respiratory airflow with respect to a reference peak airflow.

Optionally, the respiratory airflow can be a transformation of the respiratory related changes separately collected for each of the subject's nares. For example, the transformation can be a sum of a square root of a pressure signal of the respiratory airflow separately collected for each of the subject's nares.

An example method for assessing a respiratory airflow in a subject can include receiving respiratory airflow separately from each of the subject's nares, detecting a pressure of the respiratory airflow received separately from each of the subject's nares and calculating the subject's respiratory airflow as a transformation of the pressure changes received separately from each of the subject's nares. The transformation can be a sum of a square root of the pressure of the respiratory airflow received separately from each of the subject's nares.

A method for identifying a candidate for oral appliance therapy based on attractor behavior is also discussed herein. The method can include positioning an adjustable mandibular displacement device in an oral cavity of a subject during a test period, monitoring respiratory airflow of the subject during the test period, controlling the protrusion level of the adjustable mandibular displacement device to optimize respiratory airflow, identifying an attractor protrusion level where a small increase in the protrusion level results in an insignificant change in respiratory airflow and a small decrease in the protrusion level results in a signification change in respiratory airflow and, in response to identifying an attractor protrusion level, determining that the subject is a favorable candidate for oral appliance therapy.

For example, the insignificant change in respiratory airflow can be detected within a predetermined time from the small increase in the protrusion level. Optionally, the method can include determining that an effective protrusion level for oral appliance therapy is approximately the attractor protrusion level. Additionally, in response to not identifying an attractor protrusion level, the method can include evaluating an outcome of oral appliance therapy based on a history of movement of the adjustable mandibular displacement device and one or more respiratory events during the test period.

A method for performing a titration for oral appliance therapy using a multi-test-period protocol is discussed herein. The method can include positioning an adjustable mandibular displacement device in an oral cavity of a subject, monitoring the subject for one or more physiological responses during a first test period, adjusting a protrusion level of the adjustable mandibular displacement device during the first test period, establishing a recommendation for oral appliance therapy based on the titration of the protrusion level of the adjustable mandibular displacement device during the first test period and testing the recommendation for oral appliance therapy during a second test period. For instance, the physiological responses may be respiratory events or changes in airflow.

Optionally, the second test period can be subsequent to the first test period. For example, the first test period can be sleep during a first session, and the second test period can be sleep during a second session. Optionally, the first test period can be sleep during a first night, and the second test period can be sleep during a second night. Alternatively or additionally, the use of a second test period can be to include the use of other therapeutic conditions to further refine a prediction of therapeutic outcome. For example, a first test period can include sleep in one of a supine or lateral position, and the second test period can include sleep in the other of the supine or lateral position. Optionally, the second test period can include sleep with a different therapeutic intervention than the first test period. For example, the therapeutic intervention during the first test period and the second test period can be at least one of an oral appliance, a different amount of occlusal separation or an oral appliance used in conjunction with CPAP.

Optionally, testing the recommendation for oral appliance therapy can include monitoring the subject for one or more physiological responses during the second test period. The recommendation for oral appliance therapy can be confirmed, compared, refined or rejected based on the physiological responses during the second test period.

In addition, establishing a recommendation for oral appliance therapy can include identifying a range of effective protrusion levels for oral appliance therapy during the first test period. Optionally, testing the recommendation for oral appliance therapy can include adjusting the protrusion level of the adjustable mandibular displacement device within the range of effective protrusion levels during the second test period. The method can also include identifying an effective protrusion level for oral appliance therapy based on the adjustment of the protrusion level of the adjustable mandibular displacement device during the second test period.

Alternatively or additionally, establishing a recommendation for oral appliance therapy can include identifying an effective protrusion level for oral appliance therapy during the first test period. In addition, testing the recommendation for oral appliance therapy can include fixing, or minimally adjusting, the adjustable mandibular displacement device at the effective protrusion level during the second test period.

Optionally, the method can include providing a measure of predicted therapeutic outcome for oral appliance therapy. For example, the measure of predicted therapeutic outcome can be at least one of an Apnea-Hypopnea Index, a Mean $O_2$ Saturation, and Inspiratory Flow Limitation Index or a Respiratory Disturbance Index. For example, the measure of predicted therapeutic outcome can be determined at the protrusion level tested in the second test period In another implementation, a multi-test-period protocol for titrating for oral appliance therapy can include positioning an adjustable mandibular displacement device in an oral cavity of a subject, monitoring the subject for one or more physiological responses during a first test period, adjusting a protrusion level of the adjustable mandibular displacement device during the first test period, monitoring the subject for one or more physiological responses during a second test period and comparing results of monitoring the subject for one or more physiological responses during the first test period with results of monitoring the subject for one or more physiological responses during the second test period. For instance, the physiological responses may be respiratory events or changes in airflow.

Optionally, the second test period can be subsequent to the first test period. For example, the first test period can be sleep during a first session, and the second test period can be sleep during a second session. Optionally, the first test period can be sleep during a first night, and the second test period can be sleep during a second night. Alternatively or additionally, the use of a second test period can be to include the use of other therapeutic conditions to further refine a prediction of therapeutic outcome. For example, a first test period can include sleep in one of a supine or lateral position, and the second test period can include sleep in the other of the supine or lateral position. Optionally, the second test period can include sleep with a different therapeutic intervention than the first test period. For example, the therapeutic intervention during the first test period and the second test period can be at least one of an oral appliance, a different amount of occlusal separation or an oral appliance used in conjunction with CPAP.

Optionally, the method can further include adjusting the protrusion level of the adjustable mandibular displacement device during the second test period. Alternatively or additionally, the method can further include establishing a recommendation for oral appliance therapy based on the adjustment of the protrusion level of the adjustable mandibular displacement device during the first test period, and confirming, comparing, refining or rejecting the recommendation for oral appliance therapy based on the based on the adjustment of the protrusion level of the adjustable mandibular displacement device during the second test period.

In another implementation, a multi-test-period protocol for titrating for oral appliance therapy can include positioning an adjustable mandibular displacement device in an oral cavity of a subject, monitoring the subject for one or more physiological responses during a first test period, adjusting a protrusion level of the adjustable mandibular displacement device during the first test period, monitoring the subject for one or more physiological responses during a second test period and assessing results of monitoring the subject for one or more physiological responses during the first test period and results of monitoring the subject for one or more physiological responses during the second test period. For instance, the physiological responses may be respiratory events or changes in airflow.

For example, assessing results of monitoring the subject for one or more physiological responses during the first test period and results of monitoring the subject for one or more physiological responses during the second test period can include averaging the results of monitoring the subject for one or more physiological responses during the first test period and the results of monitoring the subject for one or more physiological responses during the second test period.

The method can further include establishing a recommendation for oral appliance therapy based on the assessed results.

It should be understood that the above-described subject matter may also be implemented as a computer-controlled apparatus or system, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

Figure 1A:
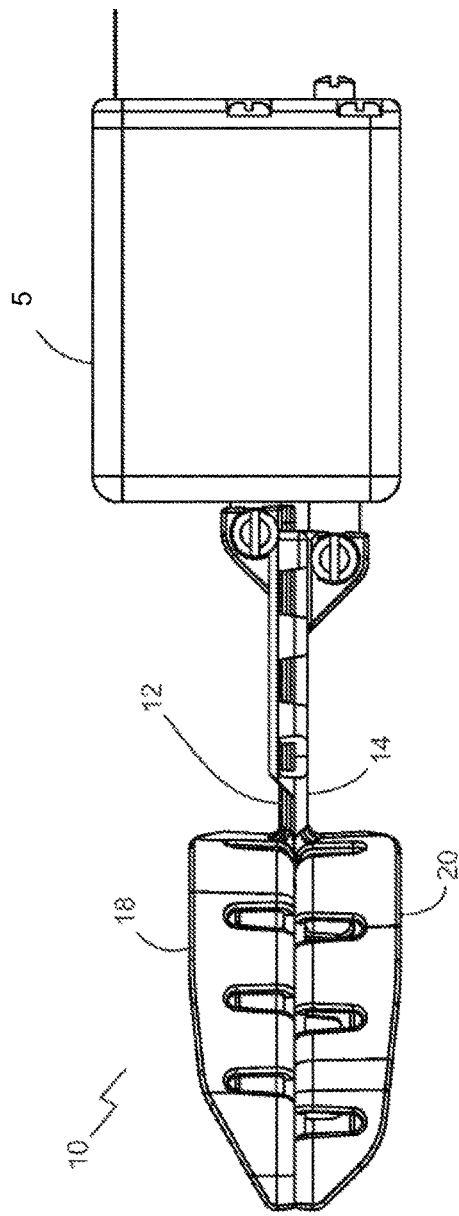
FIG. 1A illustrates an adjustable mandibular displacement device according to implementations discussed herein.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a", "an", "the", include plural referents unless the context clearly dictates otherwise. The term "comprising" and variations thereof as used herein is used synonymously with the term "including" and variations thereof and are open, non-limiting terms. While implementations will be described for performing titrations for oral appliance therapy, it will become evident to those skilled in the art that the implementations are not limited thereto.

Provided herein are methods, systems and devices for titrating or for performing one or more titrations for oral appliance therapy. A titration can be used for evaluating the effect of repositioning the subject's mandible. Optionally, a titration can be used for an evaluation of outcome of oral appliance therapy. Optionally, a titration can provide a prediction of therapeutic outcome with oral appliance therapy. A titration can be an analysis performed prior to prescribing or providing oral appliance therapy. Alternatively or additionally, a titration can be performed periodically to assess, reassess or optimize the therapeutic effectiveness of oral appliance therapy. A titration can optionally be used to identify candidates suitable for oral appliance therapy, for instance, candidates for whom the number of respiratory disturbances is below a predetermined threshold, or for whom obstructions have been reduced or eliminated to a level deemed to provide a suitable therapeutic effect. A titration can also optionally be used to identify a clinically-beneficial orientation of the mandible or a target positioning of the mandible that is deemed to provide the suitable therapeutic effect for oral appliance therapy. For example, the target positioning of the mandible can be an effective protrusion level that reduces or eliminates respiratory disturbances and obstructions to an acceptable level. A titration can also optionally be used to identify an optimal target positioning of the mandible for oral appliance therapy. A titration optionally includes evaluating the position and/or orientation of the mandible relative to the maxilla of a subject. A titration can optionally include, or be used in conjunction with, monitoring feedback signals (e.g., respiratory airflow, oxygen saturation, sound, etc.) from the subject. A titration can optionally be performed at one or more positions and/or orientations of the mandible relative to the maxilla. Titrations can optionally be used to compare target positioning of the mandible obtained during two or more titrations performed under different conditions, such as titrations performed with the use of oral appliances having varying occlusal separations, titrations performed with the subject sleeping in varying body positions, etc.

A position and/or orientation of the subject's mandible can be adjusted during a titration (e.g., automatically during the titration) or at the start of each distinct titration or distinct test period of the same titration. A target positioning of the mandible, such as one that reduces or eliminates one or more symptoms or manifestations of a sleep disorder or condition, can be provided as a specific position (e.g., a specific protrusion level) that provides a therapeutic effect for the subject. Alternatively, the target positioning can be provided as a therapeutic zone, or range of positions, within which the subject will be provided with a therapeutic treatment. The therapeutic zone can also be provided as a map that describes the effect of position other than to the optimal reposition on the subject's airway.

The clinically-beneficial orientation or effective target positioning can optionally be predetermined in a sleep test by use of a titration system. The system is used to obtain a data set representing the clinically-beneficial orientation. For example, the system is used to obtain the data set by fitting a temporary oral appliance to the subject's teeth, incrementally and reversibly advancing the subject's mandible in the anterior-posterior direction with respect to the maxilla while the subject is sleeping and collecting physiological data. The system can include an adjustable mandibular displacement device (e.g., a titration device) such as the RCMP device discussed above. The titration device can be used to titrate the optimal position of the mandible for removal of the obstruction. The titration device can be used in the clinical setting by a technician to advance the mandible until the feedback signals (e.g., respiratory airflow, $O_2$ saturation, sound, etc.) indicate removal of the obstruction. Alternatively, the titration device can be automatically adjusted (e.g., without action by a technician) using automated algorithms to adjust the position automatically based on feedback signals. Optionally, the technician can be completely absent such as when the titration is performed in a non-clinical setting, for example, in the subject's home. Optionally, the technician can be present and optionally observing the subject during the titration while the remote-controlled mandibular displacement device is adjusted without action from the technician. Optionally, the technician can operate the titration device in a clinical setting that utilizes the automated algorithms to guide or control the titration with some level of participation or monitoring from the technician. These data can be used to establish a data set from when the mandible is in a clinically-beneficial orientation relative to the maxilla.

As discussed herein, the test period can be while the subject is sleeping. There are advantages to performing a titration for oral appliance therapy while the subject is sleeping. When the test period is while the subject is sleeping, it is possible to collect data during a plurality of conditions (e.g., sleep in lateral or supine positions, REM or non-REM sleep, periods of obstruction, etc.), which can change during the night. These conditions can include a subject's worst case of obstruction. Additionally, if the test period is while the subject is sleeping, the anatomy and function of the subject's airway during the titration is the same as the anatomy and function of the subject's airway when the oral therapy is applied. For example, during sleep the muscles are in various states of relaxation which affects the configuration and response of the subject's airway. The test period can be a single sleep session. Optionally, the test period can include multiple sleep sessions. Alternatively or additionally, the test period and/or one or more of the sleep sessions can be at least 5 hours. The test period can optionally have a duration less than one night or can optionally have a duration of an entire night. A titration can also optionally include multiple test periods.

Example Titration System

Referring now to FIG. 1A, an adjustable mandibular displacement device 10 (e.g., a titration device) according to implementations discussed herein is shown. Remotely controlled adjustable mandibular displacement devices are known in the art. For example, U.S. Pat. No. 5,826,579 describes a remotely-controlled mandibular repositioner that is controlled by a technician, and U.S. Pat. No. 6,273,859 describes a remotely-controlled mandibular repositioner that is adaptively controlled by a computer. Although implementations are discussed herein with regard to the adjustable mandibular displacement device 10 shown in FIG. 1A, it should be understood that other titration devices are contemplated. For example, a titration device may be any device that has capability to reposition the mandible.

As shown in FIG. 1A, the adjustable mandibular displacement device 10 includes an upper tray 18 and a lower tray 20. The upper and lower trays 18 and 20 are attachable to an upper bracket 12 and a lower bracket 14, respectively. Additionally, the adjustable mandibular displacement device 10 includes a motor and linear actuator such as a brushless DC motor and linear actuator, which are provided in a housing 5. The specifications of the motor and linear actuator can be selected to limit a maximum travel distance (e.g., to provide a maximum of 12 mm of mandibular protrusion) and/or a maximum amount of force applied to a subject's teeth (e.g., 2.5 kg), for example. The motor and linear actuator are configured to precisely adjust the relative position of the upper and lower brackets 12 and 14. In addition, the upper and lower brackets 12 and 14 can be manually mechanically adjusted to position the upper and lower trays 18 and 20 to closely approximate a fully-retruded position of a subject's mandible. The fully-retruded position can be determined by investigation during a clinical visit prior to the titration. Thus, at the beginning of the titration, the linear actuator can be set at the fully withdrawn position when the mandible is fully-retruded. By actuating the DC motor and linear actuator, it is possible to adjust the relative position of the upper and lower brackets 12 and 14, and therefore, the relative position of the upper and lower trays 18 and 20. This exerts a force on a subject's lower jaw (mandible) to either protrude or retrude it relative to the subject's upper jaw (maxilla).

The upper and lower trays 18 and 20 can be fabricated for the subject's upper and lower teeth. This allows a close fitting of the upper and lower trays 18 and 20 to the subject's teeth so that a minimum amount of material occupies the inner surface of the teeth, which minimizes encroachment on the lingual space. This facilitates obtaining a high predictive accuracy of the titration because encroachment on the lingual space modifies the tongue position so that the oral mechanics during the titration do not mimic that which occurs when the therapeutic, custom-fitted oral appliance is used.

Figure 1B:
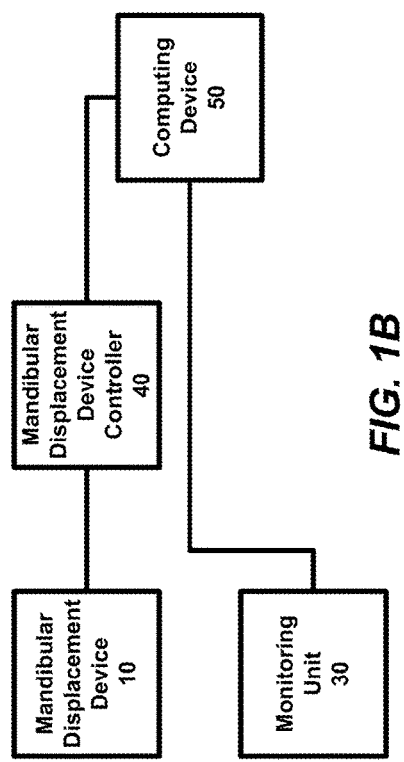
FIG. 1B is a block diagram of a titration system according to implementations discussed herein.

Referring now to FIG. 1B, a block diagram of a titration system is shown. The system can include the adjustable mandibular displacement device 10 (shown also in FIG. 1A), a monitoring unit 30, a mandibular displacement device controller 40 and a computing device 50. It should be understood that the system shown in FIG. 1B is only one example system and that a system including additional or fewer features can be provided. For example, the titration system can be implemented in a cloud computing environment to provide remote access to the components of the system. Cloud computing is a model for enabling network access to a shared pool of configurable computing resources (e.g., networks, servers, storage, applications, and services) that can be provisioned and released with minimal interaction. The cloud computing model promotes high availability, on-demand self-services, broad network access, resource pooling and rapid elasticity. It should also be understood that the communication links connecting the adjustable mandibular displacement device 10, the monitoring unit 30, the mandibular displacement device controller 40 and the computing device 50 can be any type of communication link that facilitates data communication, including, but not limited to, wired, wireless and optical communication links. For example, the adjustable mandibular displacement device 10 can be communicatively connected to the mandibular displacement device controller 40, for example, through a highly flexible, thin wire over which data including control signals are communicated between the motor and linear actuator of the adjustable mandibular displacement device 10 and the mandibular displacement device controller 40. During a titration, the mandibular displacement device controller 40 can be placed on a bedside table, for example.

In addition, the mandibular displacement device controller 40 can be communicatively connected with the computing device 50. The computing device 50 can optionally be integrated with the mandibular displacement device controller 40 as a single unit. The computing device 50 can optionally be any type of computing device such as a laptop computer, desktop computer, tablet device, or any other type of portable computing device. For example, the mandibular displacement device controller 40 can be configured to communicate data including a position of the adjustable mandibular displacement device 10 to the computing device 50. The computing device 50 can be located near the subject, as in either bedside or elsewhere within the subject's home or the treatment facility, or can be located remotely, as at the site of the manufacturer, and accessed via a network (e.g., the Internet). Optionally, aspects of the computing device 50 and/or the mandibular displacement device controller 40, such as those that control the positioning of the mandibular displacement device can be located locally, while other aspects of the computing device 50 and/or the mandibular displacement device controller 40, such as those that make decisions on which protocol to run in the next test period, can be located remotely. The computing device 50 can be configured to store and process the data as discussed in detail below. The computing device 50 can also be configured to communicate data including control signals to the mandibular displacement device controller 40.

Additionally, the monitoring unit 30 can be communicatively connected with the computing device 50. Alternatively, the monitoring unit 30 can be part of the same unit as the mandibular displacement device controller 40 and/or the computing device 50. The monitoring unit 30 can collect one or more physiological inputs, and the monitoring unit 30 can communicate the received physiological inputs to the computing device 50 for storage and/or processing. The physiological inputs can include, but are not limited to, respiratory airflow, oxygen saturation, a force on a subject's teeth, abdominal effort, brain signals, sleep stage, sleep position, acoustic energy or vibration generated by the subject, etc. These can be received directly from the subject through instrumentation such as would be applied in a standard polysomnograph recording or a portable sleep monitor. Alternatively, the physiological inputs can be received from sensors placed on a titration device (e.g., a 3D accelerometer for detecting head position, a force sensor for detecting the force applied to the teeth, accelerometers for detecting vibration of the jaw, and a microphone for detecting snoring). The computing device 50 can also be configured to communicate data including control signals to the monitoring unit 30.

Monitoring a Subject's Physiological Data

As discussed above, it is possible to monitor (or collect, measure, detect, etc.) physiological information from a subject. For example, the subject's physiological information can be monitored during a titration for oral appliance therapy. During a titration, a number of physiological inputs or data can be received from a subject. For example, as discussed above with regard to FIG. 1B, the monitoring unit 30 can collect one or more physiological inputs, and the monitoring unit 30 can communicate the received physiological inputs to the computing device 50 for storage and/or processing. The physiological inputs can include, but are not limited to, respiratory airflow, oxygen saturation, abdominal movement, brain signaling (EEG), a force on a subject's teeth, sleep stage, sleep position, acoustic energy or vibration generated by the subject, etc. These can be received directly from the subject through instrumentation such as would be applied in a standard polysomnograph recording or a portable sleep monitor. For example, the physiological inputs can include an index of respiratory airflow as recorded with nasal prongs that record pressure in the nasal airstream, electroencephalogram (EEG), electro-oculogram (EOG), submental electromyogram (EMG), electrocardiogram (ECG), arterial oxygen saturation (oxygen saturation), volume excursion of the rib cage and abdomen, snoring sound, vibrations, force measurements and body position. The physiological inputs such as airflow may be recorded with uniquely designed nasal prongs, such as those that measure the airflow separately from each nares. In addition, the physiological inputs can include supraglottic pressure through a water-filled catheter positioned in the supraglottic space. The physiological input signals can be recorded on a polygraph (and/or magnetic recording media) and displayed to a sleep technician. Alternatively or additionally, the physiological input signals can be recorded and stored directly to the titration device. Additionally, the physiological input signals can be displayed to a sleep technician and/or used by the titration system during the titration.

Detecting Respiratory Events

As discussed above, systems and devices for titrating or for performing one or more titrations for oral appliance therapy are provided. During a titration for oral appliance therapy, a subject can experience one or more respiratory events. Optionally, one or more respiratory events can be detected, for example, in real-time as opposed to in an off-line quantitative analysis of historical data (e.g., data collected during a polysomnographic or home study). Optionally, one or more respiratory events can be detected automatically with or without input from a technician. Optionally, the protrusion level of the adjustable mandibular displacement device can be controlled in response to detecting a respiratory event. A respiratory event is a transient reduction or disturbance in breathing. A respiratory event is time-limited, e.g., it has a beginning and an end. During a respiratory event, the subject's physiological system is not in steady state. For example, one or more physiological inputs from the subject (e.g., respiratory airflow, oxygen saturation, etc.) change during a respiratory event. The physiological inputs can change without any intervention. The subject can experience arousal during a respiratory event, which can cause the respiratory event to end. In contrast, during steady state breathing, a normal amount of respiratory resistance can occur, which can be altered by intervention, for instance by manipulation of the mandible. A respiratory event can be defined and measured according to predetermined criteria (discussed below). Alternatively or additionally, a respiratory event can be a classical respiratory event (discussed below). For example, during a titration for oral appliance therapy, a respiratory event can be detected by comparing one or more physiological inputs from the subject against predetermined criteria. Optionally, the predetermined criteria can be the same or different than the criteria defining classical respiratory events. Optionally, the predetermined criteria used during the titration for oral appliance therapy can be the same or different than the predetermined criteria used in the evaluation of the data from the test period.

Optionally, a respiratory event can be more than mere evidence of obstruction such as changes in respiratory airflow, oxygen saturation, snoring sound, vibration, etc. A respiratory event can be defined and measured according to predetermined criteria. A respiratory event includes any disruption in breathing that is measured against predetermined criteria. Optionally, a respiratory event is detected by calculating the difference between a physiological input signal (e.g., airflow, oxygen saturation, snoring sound, vibration, etc.) and a reference value and comparing the difference to a threshold (e.g., at least one of the predetermined criteria). The physiological information discussed below can include one or more of the physiological input signals. The reference value can optionally be a calculated baseline value or a real-time value, for example. For example, a respiratory event can optionally be defined and measured according guidelines established by the American Academy of Sleep Physicians. Alternatively or additionally, the predetermined criteria can be established by clinical organizations and published as acceptable clinical standards or can be determined independently for a group of subjects or an individual subject. For example, the predetermined criteria can be established from data obtained during a previous sleep test and customized for an individual subject and/or groups of subjects. Alternatively or additionally, the predetermined criteria can be established by determined by experimental methods, for example by training a neural network using a gold standard. The sleep test can optionally be a titration test or a polysomnographic study or study with a portable sleep monitor used in the diagnosis and assessment of sleep disordered breathing. The predetermined criteria can optionally be programmed into the titration system.

Commonly known respiratory events (i.e., classical respiratory events) include apneas (e.g., obstructive apneas, central apneas, mixed apneas), hypopneas, Respiratory Effort-Related Arousals (RERA) and flow limited breathing, Cheyne stokes respiration, hypoventilation, snoring and flow-limited breathing. The determination of respiratory events can require a change from a baseline or reference value. The baseline or reference values can be calculated in real time. The duration of a respiratory event can vary from seconds (e.g., 5-120 seconds, for example apneas or hypopneas) to minutes (e.g., 2-30 minutes or more, for example RERAs). Classical respiratory event definitions are discussed below. For example, an apnea may be defined as a reduction in respiratory airflow greater than 90% from baseline that has a duration greater than or equal to 10 seconds, with the aforementioned airflow reduction present for at least 90% of the event. A central apnea event may also have an absence of respiratory effort. A hypopnea may be a reduction in airflow greater than 30% from baseline that has a duration greater than or equal to 10 seconds, with the aforementioned airflow reduction present for at least 90% of the event in conjunction with at least a 4% reduction in blood oxygen from baseline. Alternatively, a hypopnea may be as described above with the exception of the reduction in blood oxygen being 3% from baseline.

Respiratory events as discussed herein are not limited to classical respiratory events. For example, as discussed above, oral appliance therapy can be used reduce and/or eliminate the occurrence of respiratory events, including classical respiratory events. In other words, effective oral appliance therapy reduces and/or eliminates the occurrence of classical respiratory events. During a titration for oral appliance therapy, respiratory events, including but not limited to classical respiratory events, can be detected and actions can be taken in response to detecting respiratory events. For example, respiratory events can be defined and measured according to predetermined criteria. As discussed above, the predetermined criteria can be established by clinical organization or by clinical evidence, as well as established for individual subjects and/or groups of subjects.

Figure 2A:
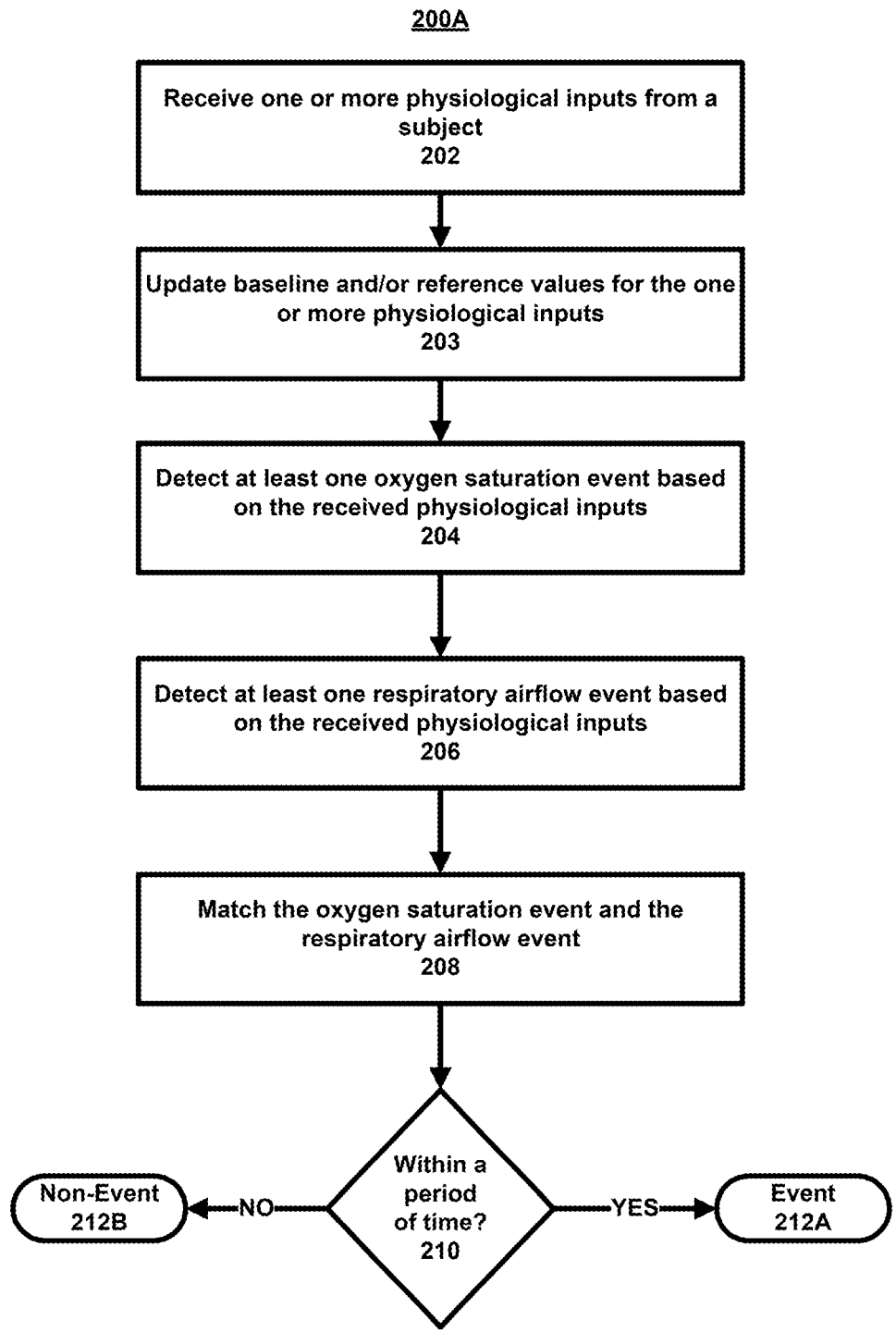
FIGS. 2A and 2B are flow diagrams illustrating example operations for detecting respiratory events.

Referring now to FIG. 2A, a flow diagram illustrating example operations 200A for detecting respiratory events is shown. Specifically, FIG. 2A illustrates example operations 200A for defining and measuring a respiratory event using predetermined criteria including a combination of oxygen saturation and respiratory airflow. Optionally, respiratory events can be defined and measured in real-time during the test period. For example, at 202, one or more physiological inputs can be received from a subject. The physiological inputs can include respiratory airflow and oxygen saturation. At 203, the reference for respiratory airflow and the baseline for oxygen saturation can optionally be updated with the inputs received at 202. Example methods for calculating baseline and reference respiratory airflow and baseline oxygen saturation are discussed below. At 204, at least one oxygen saturation event can be detected based on the received physiological inputs. For example, oxygen saturation events can be detected based on the deviation from the baseline oxygen saturation updated at 203. Additionally, at 206, at least one respiratory airflow event can be detected based on the received physiological inputs. For example, respiratory airflow events can be detected based on the deviation from the reference airflow updated at 203. Then, at 208, the oxygen saturation event and the respiratory airflow event can be matched. At 210, a determination is made as to whether the oxygen saturation event and the respiratory airflow event are detected within a period of time (e.g., the events occur within a predetermined time lag). For example, a determination can be made as to whether the oxygen saturation event is detected within a predetermined period of time after the respiratory airflow event is detected. If YES, at 212A, the matched oxygen saturation event and respiratory airflow event are classified as a respiratory event. If NO, at 212B, the matched oxygen saturation event and respiratory airflow event are not classified as a respiratory event. After matching the oxygen saturation event and respiratory airflow event, a respiratory event can be classified in terms of severity, which can also occur in real-time. In other words, the physiological inputs can be collected from the subject concurrently with the steps of detecting and matching oxygen saturation and respiratory airflow events and classifying respiratory events. According to the implementations discussed herein it is possible to continue to receive one or more physiological inputs from the subject, which is used to identify subsequent respiratory events and to update the baseline and/or reference values.

Optionally, the matched oxygen saturation event and respiratory airflow event can be classified as a respiratory event after a test period. For example, the oxygen saturation event and respiratory airflow event can be detected as a difference from a baseline or reference values calculated from the data from the whole test period.

An oxygen saturation event can be a decrease in oxygen saturation of at least a minimum amount from baseline oxygen saturation. For example, the minimum amount can be approximately 1.5%. Thus, an oxygen saturation event is detected if oxygen saturation decreases by an amount greater than 1.5% from baseline oxygen saturation. Example methods for calculating baseline oxygen saturation are provided below. This disclosure contemplates that one of ordinary skill in the art can calculate baseline oxygen saturation by another method. Optionally, baseline oxygen saturation can be calculated as a moving average. Baseline oxygen saturation can therefore optionally be calculated for an individual subject in real-time during a titration. For example, calculating the moving average can include receiving a plurality of oxygen saturation samples during a moving average time period. Oxygen saturation can optionally be sampled at 1 Hz (e.g., 1 sample per second). The moving average time period can be any time period such as 10 seconds, for example. The moving average time period can optionally be more or less than 10 seconds. Then, one or more of the plurality of oxygen saturation samples having oxygen saturation within in an Xth percentile among the plurality of oxygen saturation samples can be averaged. The Xth percentile can be the top $25^{th}$ percentile (e.g., within the $75^{th}$ percentile) among all of the oxygen saturation samples. It should be understood that one or more of the oxygen saturation samples can be excluded from the moving average (e.g., the oxygen saturation samples having oxygen saturation outside of the Xth percentile, for example).

Alternatively or additionally, detecting an oxygen saturation event can include detecting a decrease in the real-time value of oxygen saturation of at least a minimum amount. In other words, a decrease that is not calculated from baseline oxygen saturation can be used. For example, the minimum amount can be 1.5%. Alternatively or additionally, an oxygen saturation event can be a decrease of a threshold magnitude that is achieved by a plurality of consecutive decreases in oxygen saturation followed by an increase in oxygen saturation. As discussed above, oxygen saturation can optionally be sampled at 1 Hz (e.g., 1 sample per second). For example, the plurality of consecutive decreases in oxygen saturation can include at least 3 consecutive decreases each decrease a minimum of 0.5%. Accordingly, an oxygen saturation event can be three oxygen saturation samples with consecutively decreasing oxygen saturation followed by a sample with increasing oxygen saturation.

Respiratory airflow can be detected using nasal prongs that detect pressure in the subject's nasal airstream. The detected pressure can be an absolute pressure (e.g., pressure minus ambient pressure) in the subject's nasal airstream, for example. Optionally, the pressure in each of the subject's nares can be collected separately, and respiratory airflow can be a transformation of the pressure separately collected for each of the subject's nares. For example, the transformation can be a sum of a square root of a pressure signal (e.g., absolute pressure) separately collected for each of the subject's nares.

Baseline respiratory airflow is used to characterize the breath. For example, the baseline respiratory airflow is used to determine limits and measurements of inspiration. The baseline respiratory airflow is the average airflow calculated over a relatively long period of time such as, for example, a 20 minute period. Optionally, baseline respiratory airflow can be the average pressure detected by nasal prongs in the subject's nares as discussed below. Baseline respiratory airflow can be used to identify the "zero" point of the pressure signal from which the onset and end of each breath is identified.

Baseline respiratory airflow can be used to identify the onset and end of each breath. The onset and end of inspiration are needed to calculate breath-by-breath minute ventilation and/or peak airflow. Example methods for calculating baseline respiratory airflow are provided below. This disclosure contemplates that one of ordinary skill in the art can calculate baseline respiratory airflow by another method. For example, baseline respiratory airflow can be calculated as a moving average. The baseline respiratory airflow can therefore optionally be calculated for an individual subject in real-time during a titration. Calculating the moving average can include receiving a plurality of respiratory airflow samples during a moving average time period. Respiratory airflow can optionally be sampled at 25 Hz (e.g., 25 samples per second). The moving average time period can be any time period such as 20 minutes, for example, when calculating baseline respiratory airflow. The moving average time period can optionally be more or less than 20 minutes. Then, the moving average can be calculated as a moving mode (e.g., most-common value) based on the plurality of respiratory airflow samples. Alternatively or additionally, calculating the moving average can include receiving a plurality of respiratory airflow samples during a moving average time period, and calculating the moving average as a moving median based on the plurality of respiratory airflow samples.

Real-time calculation of the baseline respiratory airflow can then be used to detect respiratory events in real time, by providing a means of detecting the onset and the end of the inspiratory interval for each detected breath. The detection of the onset and the end of the inspiratory interval are used to measure changes in the peak airflow. The change in peak airflow can be calculated for a single breath or for a plurality of breaths. The plurality of breaths can optionally be a plurality of consecutive breaths. Alternatively, the detection of the onset and the end of the inspiratory interval by real time calculation of a baseline respiratory airflow can be used to detect a change in the breath-by-breath minute ventilation. The breath-by-breath minute ventilation may be detected as a moving average value for a time period. The respiratory airflow event can optionally be detected as monotonic decrease in calculated averaged breath-by-breath minute ventilation measured from a reference respiratory airflow followed by an increase in breath-by-breath minute ventilation. The reference respiratory airflow can be, for example, calculated as a smaller from two values with the first value being the last value of averaged breath-by-breath minute ventilation before the beginning of the monotonic decrease and the second value being the value at which the rebound is completed. Alternatively, the respiratory airflow event can optionally be detected as a change in peak to peak flow.

Optionally, reference respiratory airflow can be a moving average of respiratory airflow over a period of time such as 10 seconds, for example. Optionally, reference respiratory airflow can be an average breath-by-breath ventilation of one or more breaths. Optionally, reference respiratory airflow can be the average peak respiratory airflow of one or more breaths. For instance, respiratory airflow can be averaged during a moving time period (e.g., 10 seconds). Optionally, reference respiratory airflow can be based on the pressure detected by nasal prongs in the subject's nares. Reference respiratory airflow can be used to detect a change in respiratory airflow and/or a respiratory airflow event.

A respiratory airflow event can be a monotonic decrease followed by an increase in respiratory airflow relative to a reference respiratory airflow. For example, a respiratory airflow event can be a monotonic decrease followed by an increase in breath-by-breath minute ventilation relative to a reference breath-by-breath minute ventilation. In cases where the decrease and increase in respiratory airflow are not quite monotonic, a portion of the initial decrease can be "carried over" when calculating reference respiratory airflow.

Detection of a respiratory event by changes in minute by minute ventilation are more sensitive, as it utilizes changes in both the frequency and amplitude of the breath. Similarly, there are advantages in the method of calculating a baseline respiratory airflow by a moving median as compared to calculating a moving mode. For example, differences in breathing patterns may have more effect on a moving mode. The use of airflow in determining respiratory events is not common, as typically it is not a reliable and accurate signal. According to the methods provided herein, the accuracy and reliability are increased by the calculation of a reliable baseline airflow from which the onset and end of breath can be determined. Additionally, respiratory airflow detected separately from each of the subject's nares can be more accurate as it takes into account naris-specific changes in airflow that are known to occur throughout the night. Additionally, the use of airflow in the detection of respiratory events during an oral appliance titration can be more complete and reliable because the titration device impedes respiratory airflow through the mouth. Accordingly, air taken in through the subject's nose has difficulty escaping through the subject's mouth, which makes the detected respiratory airflow more complete and reliable.

As discussed above, a respiratory event is classified if the oxygen saturation event is detected within the predetermined time lag (e.g., a fixed or customized time lag) after the respiratory airflow event is detected. Optionally, the predetermined time lag can be fixed for all subjects. For example, the predetermined time lag can be between approximately 10-40 seconds (e.g., 25±15 seconds). Optionally, the predetermined time lag, or the period of time between matched oxygen saturation and respiratory airflow events, can be subject-specific. The time lag can optionally be customized in terms of its range (e.g., the width of the correlation period) and the value of its midpoint (e.g., the position of the correlation window). The value of the midpoint determines the interval of time between the oxygen saturation event and the preceding respiratory airflow event and the range, evenly distributed on both sides of the midpoint, determines the time window in which the preceding respiratory airflow event must be located (i.e., occur) in order to be correlated with the subsequent oxygen saturation event. For example, the customized time lag can be a time lag that provides the greatest number of matched respiratory events between oxygen saturation events and airflow events collected during a time period. For example, the customized time lag can be identified by summing the number of respiratory events detected during each fixed time interval for varying midpoint values of lag time. For example, calculating the number of events with a 30 second range on either side (e.g., ±15 seconds) of starting value and comparing it with the number of events during the same 30 second window at successive positions (e.g., starting time interval plus 1 second, 2 second, 3 seconds, etc.), identifying the position of time with the greatest number of respiratory events and accepting a range on either side of the identified interval of time (e.g., ±15 seconds, for example). For example, a time interval of 30 seconds may be initially selected. The number of events detected with a matching time interval from 5 seconds to 35 seconds would be compared with the number of events detected with a matching time interval from 6 to 36 seconds, 7 to 37 seconds, etc. and the interval with the greatest number of respiratory events would be accepted. Determination of the customized time lag could also involve changing the width of the correlation window. It should be understood that the customized time lag can be used in real-time analysis of the respiratory events or off line when re-scoring the respiratory events in the data collected with a fixed time lag for use in the prediction algorithms discussed herein. Additionally, the fixed time lag can optionally be used in a first phase of data collection and then the customized time lag can be used in a second phase of data collection. For example, the customized time lag can be determined in a first night and then utilized in a second night, or the customized time lag can be determined in a first portion of the test period and then utilized in the second portion of the same test period. The customized time lag can optionally be calculated off line or in real time. Alternatively, the predetermined time lag can be customized for an individual subject by collecting data using a fixed time lag and then analyzing the respiratory response to determine the customized time lag. The analysis can be performed before conducting a titration for oral appliance therapy on the subject. Alternatively or additionally, the analysis can be performed while conducting a titration for oral appliance therapy on the subject.

Figure 2B:
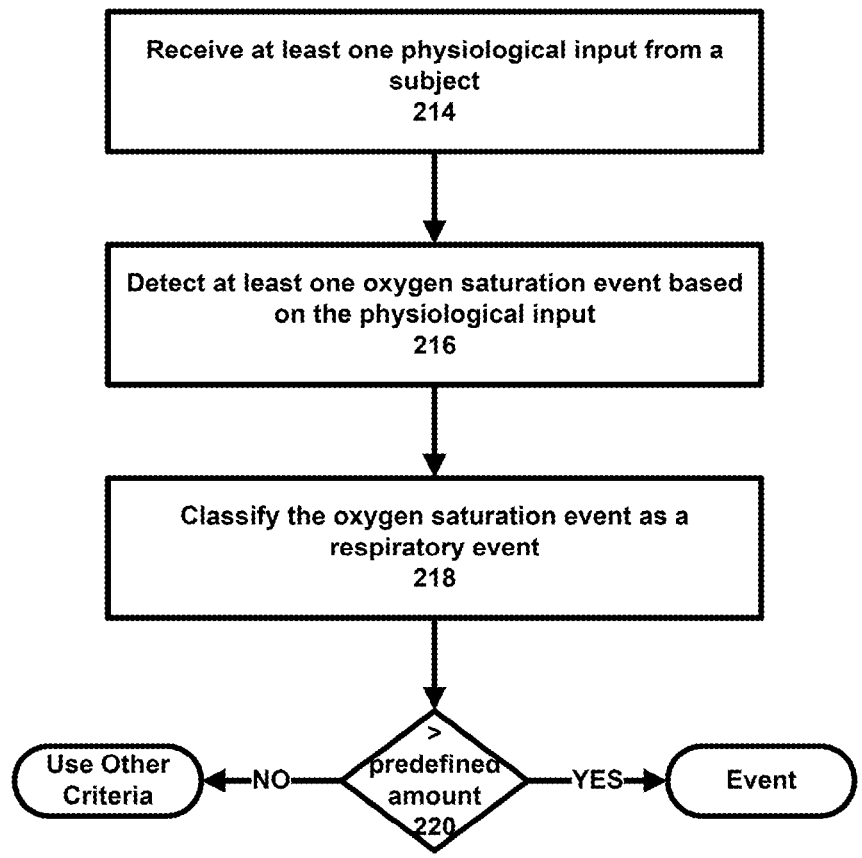

Referring now to FIG. 2B, a flow diagram illustrating example operations 200B for detecting respiratory events is shown. Specifically, FIG. 2B illustrates example operations 200B for defining and measuring a respiratory event using oxygen saturation. For example, a respiratory event can optionally be classified based only on a large decrease in oxygen saturation from real-time or baseline oxygen saturation. At 214, at least one physiological input can be received from a subject. The physiological input can be oxygen saturation, for example. At 216, at least one oxygen saturation event is detected based on the received physiological input. Then, at 218, the oxygen saturation event is classified as a respiratory event. In particular, at 220, a determination as to whether a decrease in oxygen saturation exceeds at least a predefined amount from real-time or baseline oxygen saturation. For example, the predefined amount can be approximately 6%. If YES, the oxygen saturation event is classified as a respiratory event. If NO, it is not possible to detect a respiratory event using only oxygen saturation. Optionally, respiratory events can be detected using other predetermined criteria. For example, respiratory events can be define and measured using predetermined criteria including a combination of oxygen saturation and respiratory airflow as discussed above with regard to FIG. 2A.

Figure 2C:
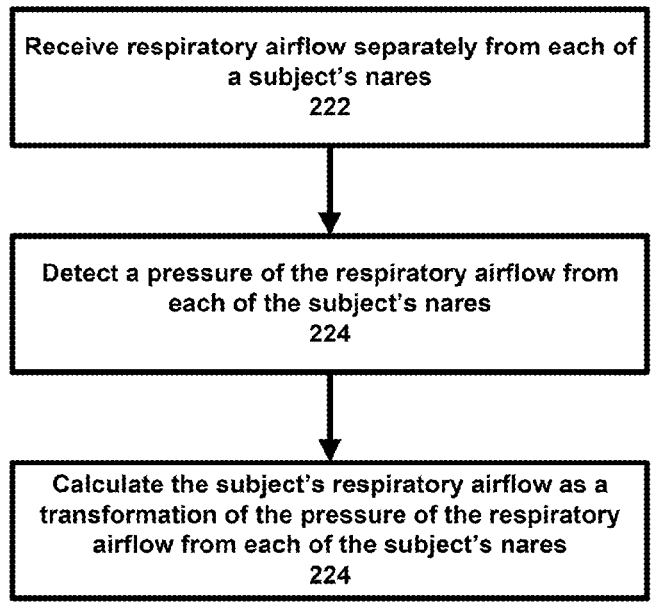
FIG. 2C is a flow diagram illustrating example operations for assessing respiratory airflow in a subject.

Referring now to FIG. 2C, a flow diagram illustrating example operations 200C for assessing respiratory airflow in a subject is shown. As discussed above, respiratory airflow can be detected using nasal prongs that detect pressure in the subject's nasal airstream. For example, a cannula having separate tubes for each of the subject's nares can be used to collect respiratory airflow separately from each of the subject's nares. The recorded pressure can be an absolute pressure (e.g., pressure minus baseline pressure) in the subject's nasal airstream, for example. At 222, respiratory airflow can be separately collected from each of the subject's nares. At 224, a pressure signal from each of the subject's nares can be detected. Then, at 226, the subject's respiratory airflow can be calculated as a transformation of the pressure signals received separately from each of the subject's nares. For example, the transformation can be a sum of a square root of a pressure signal (e.g., absolute pressure) separately collected from each of the subject's nares. The calculated respiratory airflow can be used to estimate peak respiratory airflow, breath-by-breath minute ventilation or any other useful measure. The respiratory airflow can be used to detect a respiratory airflow event, used in the detection of a respiratory event, or may be used to assess the effect of repositioning the mandible.

Alternatively or additionally, detecting a respiratory event can include detecting an occurrence of inspiratory flow limitation. This occurrence can be determined by comparison to parameters established using a neural network trained against a gold standard. The inputs can include at least one of oxygen saturation, respiratory airflow, acoustic energy (sound) and vibration energy or combinations thereof.

Controlling a Protrusion Level of the Titration Device

As discussed herein, controlling a protrusion level includes repositioning a subject's mandible relative to the maxilla in at least one degree of freedom. For example, the subject's mandible can be moved in the anterior-posterior direction relative to the maxilla. Additionally, controlling a protrusion level includes repositioning the subject's mandible relative to the maxilla in two, three, four, five or six degrees of freedom. For example, the subject's mandible can be moved relative to the maxilla by adjusting the amount of bite opening (e.g., rotation of the mandible around the condyle) and/or separation of the teeth (e.g., parallel separation of the condyle). For multidimensional titration, a titration device can be used to adjust the position of the mandible in a plurality of degrees of freedom. For example, in addition to adjusting the protrusion level of the mandible in the anterior-posterior direction, the position can be adjusted for separation between the occlusal surfaces of the teeth and can also be adjusted for the amount of bite opening. In these instances the therapeutic position, or clinically-beneficial orientation, is optionally described in multiple variables, and the therapeutic zone, including the clinically-beneficial orientation, is optionally provided as a three dimensional map.

As discussed above, it is possible to alter the protrusive distance of the mandible relative to the maxilla in the anterior-posterior direction (e.g., translation of the mandible relative to the maxilla in the anterior-posterior direction). Protrusion of the mandible relative to the maxilla in the anterior-posterior direction lengthens anterior pharyngeal muscles and tends to open the pharynx.

It is also possible to alter and maintain the bite opening of the subject, which is a rotational movement of the mandible around the condyle. This rotation opens the bite and displaces the mandible posteriorly and caudally, which has implications for the treatment of sleep apnea as a number of pharyngeal muscles (e.g., genioglossus, geniohyoid, stylosglossus, etc.) either directly or indirectly attach to an anterior region of the mandible. The effects of the mandible's rotation on the mechanics of the passive pharynx demonstrate that rotation increases closing pressure and reduces maximum cross-sectional area of the airway.

While the temporomandibular (T-M) joint has two primary movements (e.g., translation (or protrusion) and rotation), a smaller form of vertical adjustment is also optionally used. Parallel separation (e.g., caudal movement of the condyle in the absence of translation) is limited (e.g., 1 to 3 mm, for example) and a small separation of the T-M joint surface represents the normal, unloaded condition of the joint. Thus, in the mandibular protruded situation, the joint surfaces should be separated. This is particularly important during long term position or bruxism, when loading of the T-M joint by apposition of the surfaces may cause pain and produce joint deterioration. This movement provides additional space for the tongue.

Therefore, repositioning in any of these three dimensions (e.g., protrusion, bite opening or parallel separation) has therapeutic effect. It should be understood that each of these three dimensions can be independently considered in determining the predetermined clinically-beneficial orientation.

Systems and methods are provided herein for automatically controlling a titration device such as the adjustable mandibular displacement device 10 discussed with regard to FIG. 1A. Example implementations are provided with respect to the adjustable mandibular displacement device 10. It should be understood that this disclosure contemplates that the protrusion level of other titration devices can also be controlled. For example, the adjustable mandibular displacement device 10 can be an automatically-controlled mandibular protruder. An automatically-controlled mandibular protruder can be dynamically adjusted without having a technician manually adjust the mandibular displacement device locally (e.g., at or adjacent to the subject's oral cavity) and can be dynamically adjusted without technician control or can be dynamically adjusted by a technician with automatically generated prompts that help the technician guide the titration.

Optionally, controlling a protrusion level of the adjustable mandibular displacement device can include adjusting the protrusion level of the adjustable mandibular displacement device based on at least one of frequency or severity of one or more respiratory events. For example, the protrusion level can be dynamically and automatically controlled (e.g., in real-time) during a titration based on the frequency or severity of the respiratory events. Alternatively or additionally, a protrusion level of the adjustable mandibular displacement device can be controlled to induce one or more respiratory events or to induce a change in respiratory airflow. Alternatively or additionally, a protrusion level of the adjustable mandibular displacement device can be controlled to optimize a protrusion level.

Figure 3:
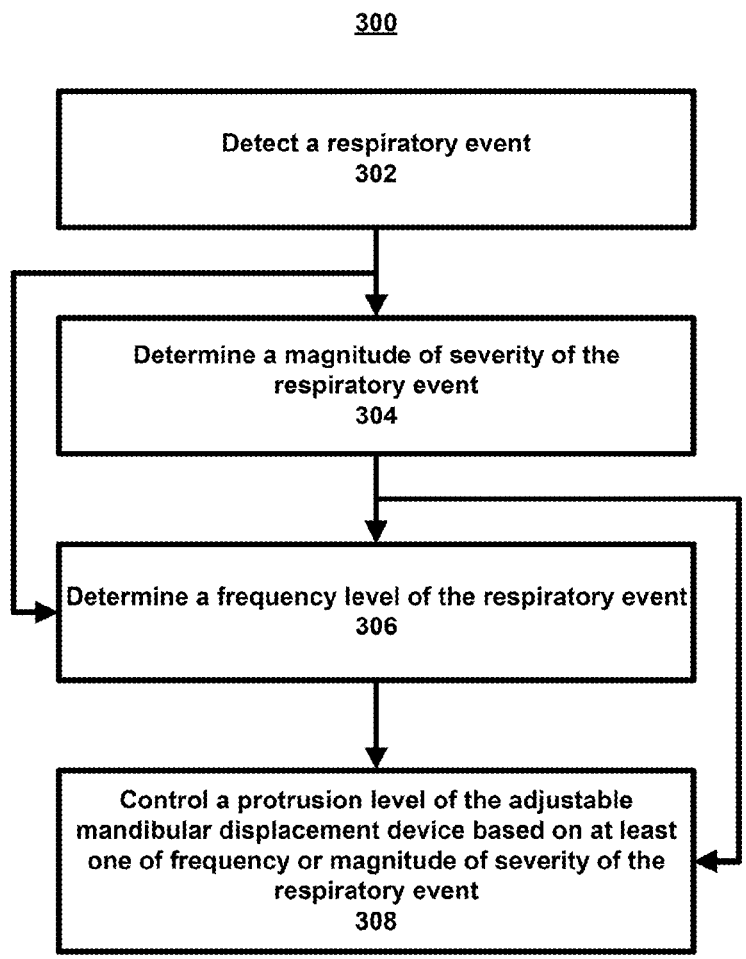
FIG. 3 is a flow diagram illustrating example operations for controlling a protrusion level of the adjustable mandibular displacement device based on frequency or severity of respiratory events.

Referring now to FIG. 3, a flow diagram illustrating example operations 300 for controlling a protrusion level of the adjustable mandibular displacement device based on frequency or severity of respiratory events is shown. It should be understood that controlling a protrusion level of the adjustable mandibular displacement device can include at least one of increasing or decreasing the protrusion level of the adjustable mandibular displacement device. For example, at 302, a respiratory event can be detected. Detection of respiratory events is discussed in detail above. For example, detecting a respiratory event can include defining and measuring physiological information from a subject against predetermined criteria. At 304, a magnitude of severity of the respiratory event can be determined. The magnitude of severity can be calculated by assessing the severity of one or both of airflow event and an oxygen event. Alternatively or additionally, a frequency of respiratory events (e.g., respiratory events/unit time) can be calculated. Optionally, a frequency of respiratory events of each magnitude of severity can be determined. And, at 306, a frequency level of the respiratory event can be determined. At 308, the protrusion level of the adjustable mandibular displacement device can be controlled based on at least one of the magnitude of severity or frequency of the respiratory event. For example, at least one of a magnitude and rate of adjustment can be related to at least one of frequency or magnitude of severity of the respiratory event. Alternatively or additionally, both the magnitude and rate of adjustment can be related to at least one of a frequency or magnitude of severity of the respiratory event. The magnitude of adjustment is the amount (e.g., number of millimeters) the protrusion level of the adjustable mandibular displacement device is adjusted. For example, the protrusion level can be adjusted by 5 mm in response respiratory events of a given severity and/or frequency level. The rate of adjustment defines how fast (or slow) the protrusion level of the adjustable mandibular displacement device is adjusted. For example, the protrusion level can be adjusted by 5 mm after a period of delay, for instance a 1 minute delay, or alternatively without a period of delay in response respiratory events of the given severity and/or frequency level. In particular, a higher magnitude or rate of adjustment can correspond to a more frequent or severe respiratory event, and a lower magnitude or rate of adjustment can correspond to a less frequent or severe respiratory event. Accordingly, it is possible to adjust the protrusion level rapidly through protrusion levels at which more severe or frequent respiratory events are occurring and settle at a larger protrusion level range where less severe or frequent respiratory events occur. Then, it is optionally possible to optimize the protrusion level within the protrusion level range where less severe or frequent respiratory events occur. The optimization may be done by monitoring and adjusting for the magnitude of airflow.

The magnitude of the severity of the one or more respiratory events can optionally be determined as discussed below. The magnitude of severity can optionally be classified into one of a plurality of predetermined categories. For example, when the physiological inputs from the subject include oxygen saturation and respiratory airflow, oxygen saturation events and respiratory airflow events can be identified, and oxygen saturation events can be matched with corresponding respiratory airflow events to identify respiratory airflow events. The categories therefore can include a plurality of categories related to a severity of the oxygen saturation event and a plurality of categories related to a severity of the respiratory airflow event. For example, a decrease in oxygen saturation associated with the respiratory event can be classified into one of n categories, and a decrease in respiratory airflow associated with the respiratory event can be classified into one of m categories. The magnitude of the severity of a respiratory event can be determined using an n×m matrix based on the severities of the decrease in oxygen saturation and the decrease in respiratory airflow associated with the respiratory event, where n and m are integers>1. At least one of a magnitude and a rate of adjustment of the protrusion level can be controlled based on the magnitude of the severity determined using the n×m matrix.

For example, there can be three categories for a severity level of the respiratory airflow event (e.g., m=3). A first category can correspond to approximately an 80-100% decrease in respiratory airflow. A second category can correspond to approximately a 45-79% decrease in respiratory airflow. A third category can correspond to approximately a 30-44% decrease in respiratory airflow. A decrease in respiratory airflow that does not fall within one of the categories above, for example a decrease of less than approximately 30%, is not registered as a respiratory airflow event and is considered a normal fluctuation in breathing. Alternatively or additionally, there can be three categories for a magnitude of severity of the oxygen saturation event (e.g., n=3). A first category can correspond to an approximately 6% or greater decrease in oxygen saturation from real-time or baseline oxygen saturation. A second category can correspond to an approximately 3-6% decrease in oxygen saturation from real-time or baseline oxygen saturation. A third category can correspond to an approximately less than 3% decrease in oxygen saturation from real-time or baseline oxygen saturation. It should be understood that the values of m and n, as well as the values for each of the categories, are provided only as examples, and that other values can be used.

Additionally, the frequency level of the one or more respiratory events can optionally be determined. The frequency level of the one or more respiratory events can be used to determine at least one of the magnitude and rate of adjustment of the adjustable mandibular displacement device. For example, a magnitude of the severity of the respiratory event can be determined as discussed above (e.g., using the n×m matrix). Optionally, a frequency at which the respiratory event occurs is calculated. The frequency at which the respiratory event occurs can be multiplied by the magnitude of the severity level of the respiratory event to obtain a frequency-severity index. The protrusion level of the adjustable mandibular displacement device can be controlled based on the frequency-severity index. Optionally, the frequency of respiratory events having substantially the same magnitude of severity are determined and then multiplied by the magnitude of severity to obtain a frequency-severity index. A global frequency-severity index can be calculated by summing the frequency-severity indexes for a plurality of respiratory events. The protrusion level of the adjustable mandibular displacement device can be controlled during the test period based on the global frequency-severity index.

Alternatively or additionally, a frequency level of the respiratory event can be classified into one of q categories and a frequency-severity index can be obtained using an n×m×q matrix based on the severity and frequency levels associated with the respiratory event, where n and m and q are integers>1. The protrusion level of the adjustable mandibular displacement device can be controlled based on the frequency-severity index.

Automated Titration for Oral Appliance Therapy

Figure 4:
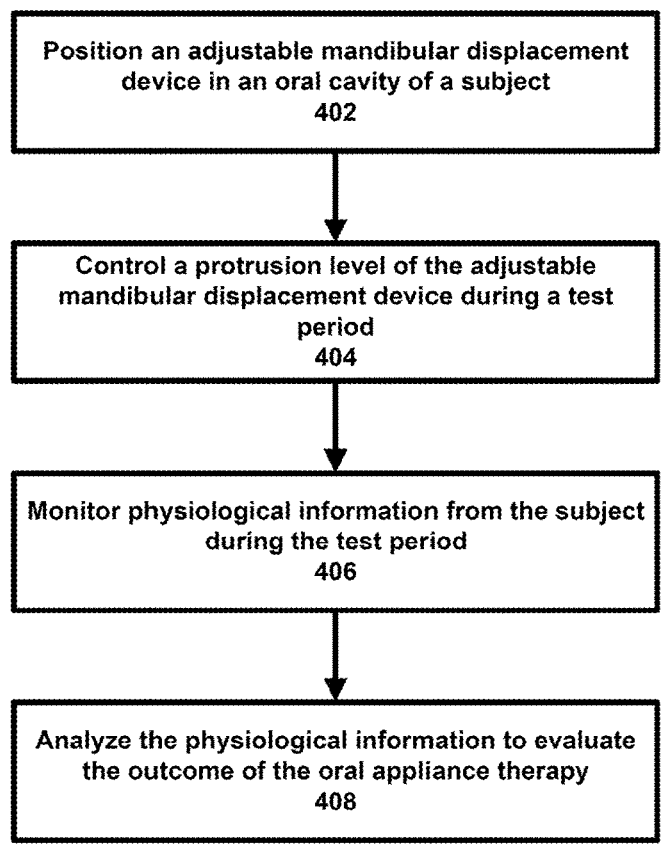
FIG. 4 is a flow diagram example operations for evaluating an outcome of oral appliance therapy is shown.

Referring now to FIG. 4, a flow diagram 400 illustrating example operations for evaluating an outcome of oral appliance therapy in a subject is shown. At 402, an adjustable mandibular displacement device can be positioned in an oral cavity of the subject. After placing the adjustable mandibular displacement device, an automatic titration protocol can be implemented. At 404, a protrusion level of the adjustable mandibular displacement device can be controlled during a test period. At 406, physiological information from the subject is monitored during the test period. For example, the physiological information can include respiratory airflow and oxygen saturation. The physiological information can also include other information related to a subject including, but not limited to acoustic energy or vibration generated by the subject, sleep position, sleep stage or force applied to a subject's teeth, including combinations thereof. Then at 408, the physiological information is analyzed to evaluate the outcome of oral appliance therapy.

Optionally, the evaluation can be a prediction of whether the subject is a favorable candidate for oral appliance therapy. Alternatively or additionally, the evaluation can optionally be an indication of an effective protrusion level of the adjustable mandibular displacement device. Alternatively or additionally, the evaluation can optionally be an indication of an optimal effective protrusion level of the adjustable mandibular displacement device.

The protrusion level of the adjustable mandibular displacement device can optionally be controlled during the test period based on the physiological information. Additionally, analyzing the physiological information can include processing the physiological information using a computing device. Optionally, the physiological information is analyzed to detect one or more respiratory events. For example, the relationship between one or more of components of the physiological information can be analyzed to detect (identify, classify, etc.) a respiratory event using predetermined criteria, for example, according to any of the methods discussed herein. Detection of respiratory events is discussed in detail above. For example, detecting a respiratory event includes defining and measuring physiological information from a subject against predetermined criteria. A respiratory event is more than mere evidence of obstruction (e.g., a change in respiratory airflow, oxygen saturation, snoring sound, etc.).

For example, a frequency of occurrence of the one or more respiratory events can be calculated. If the frequency of occurrence is greater than a predetermined threshold, a protrusion level of the adjustable mandibular displacement device can be controlled by increasing the protrusion level of the adjustable mandibular displacement device. The protrusion level can be increased until the frequency of occurrence of the one or more respiratory events is less than the predetermined threshold. The protrusion level can therefore be increased to minimize and/or eliminate occurrence of respiratory events to an acceptable level. Optionally, at least one of a magnitude and rate of adjustment of the protrusion level can be controlled based on frequency or severity of the respiratory events as discussed herein. Accordingly, the predetermined threshold can be selected such that the adjustable mandibular displacement device is controlled to minimize and/or eliminate respiratory events to an acceptable level when the frequency of occurrence exceeds the predetermined threshold.

Alternatively or additionally, if the frequency of occurrence of the one or more respiratory events is less than a predetermined threshold, a protrusion level of the adjustable mandibular displacement device can be controlled to optimize respiratory airflow or another physiologic input (e.g., snoring) as discussed herein. For example, a first protrusion level beyond which a decrease in the protrusion level results in a decrease respiratory airflow can be identified. For example, the first protrusion level can be a minimum protrusion level ($P_{crit}$), where a further decrease in protrusion level results in a decrease in respiratory airflow. Optionally, the average breath-by-breath minute ventilation for one or more breaths before a change in protrusion level can be compared to the average breath-by-breath minute ventilation for one or more breaths after the change in protrusion level to determine how the change in protrusion level effected respiratory airflow. Optionally, a similar comparison can be performed using peak respiratory airflow. Additionally, a second protrusion level beyond which an increase in the protrusion level does not result in an increase in respiratory airflow can also be identified. For example, the second protrusion level can be an optimal protrusion level ($P_{opt}$), where a further increase in protrusion level does not result in an increase in respiratory airflow. Optionally, the average breath-by-breath minute ventilation for one or more breaths before a change in protrusion level can be compared to the average breath-by-breath minute ventilation for one or more breaths after the change in protrusion level to determine how the change in protrusion level effected respiratory airflow. Optionally, a similar comparison can be performed using peak respiratory airflow. An effective protrusion level for oral appliance therapy can be approximately between the first protrusion level and the second protrusion level. Alternatively or additionally, a third protrusion level where a small increase in the protrusion level results in an insignificant change in respiratory airflow and a small decrease in the protrusion level results in a signification change in respiratory airflow can be identified. This response is known as attractor behavior, which is discussed in detail below. Optionally, an effective protrusion level for oral appliance therapy can be approximately the third protrusion level. Optionally, a protrusion level of the adjustable mandibular displacement device during the test period can be controlled in response to not detecting a respiratory event during a fixed period of time in order to induce a respiratory event or to induce a change in respiratory airflow.

Titrating Based on a Comprehensive Data Set

Figure 5A:
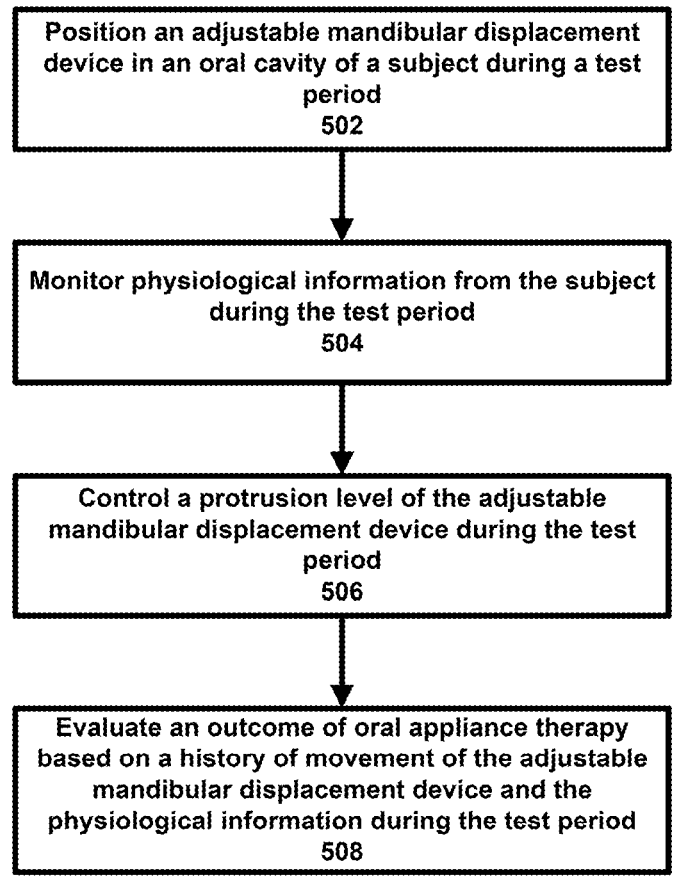
FIG. 5A is a flow diagram illustrating example operations for performing a titration for oral appliance therapy using a comprehensive data set.

Referring now to FIG. 5A, a flow diagram illustrating example operations 500A for performing a titration for oral appliance therapy using a comprehensive data set is shown. By performing a titration for oral appliance therapy using a comprehensive data set, the overall response at various protrusion levels during a test period is examined in order to evaluate therapeutic outcome. For example, as discussed below, respiratory events are detected, and in some cases even induced, and classified. Then, the protrusion level of the titration device is dynamically controlled in response to the respiratory events. The protrusion level can be controlled using a graded dynamic adjustment (e.g., magnitude and rate) according to the classified respiratory events. Therapeutic outcome can then be evaluated based on the overall data set, which includes, but is not limited to, the physiological response of the subject and information regarding the dynamic response of the titration device (e.g., how fast and how far the titration device moves during the test period).

For example, at 502, an adjustable mandibular displacement device can be positioned in an oral cavity of a subject during a test period. At 504, physiological information from the subject is monitored and recorded during the test period. For example, the physiological information can include respiratory airflow and oxygen saturation. The physiological information can also include other information related to a subject including, but not limited to, acoustic energy or vibration generated by the subject, sleep position, sleep stage or force applied to a subject's teeth, including combinations thereof. Additionally, at 506, a protrusion level of the adjustable mandibular displacement device can be controlled and recorded during the test period. The protrusion level of the adjustable mandibular displacement device can be controlled according to any of the methods discussed herein. For example, the adjustable mandibular displacement device can be controlled to reduce the frequency of respiratory events to an acceptable level. Alternatively or additionally, the adjustable mandibular displacement device can be controlled based on severity or frequency of the respiratory events. Optionally, the adjustable mandibular displacement device can be controlled to optimize airflow. The physiological information from 504 is recorded in relation to the protrusive level at which it was detected, as recorded in 506. Temporal data for each of 504 and 506 is similarly recorded. At 508, the outcome of oral appliance therapy is evaluated based on a history of movement of the adjustable mandibular displacement device and the physiological information during the test period. For example, as discussed herein, the evaluation can be a prediction of whether the subject is a favorable candidate for oral appliance therapy. Alternatively or additionally, the evaluation can optionally be an indication of an effective protrusion level of the adjustable mandibular displacement device. An effective protrusion level of the adjustable mandibular displacement device can be a protrusion level that reduces the severity or frequency of respiratory events to an acceptable level. Alternatively or additionally, the evaluation can optionally be an indication of an optimal effective protrusion level of the adjustable mandibular displacement device.

As discussed above, the monitored physiological information can include, but is not limited to, acoustic energy or vibration generated by the subject, sleep position, sleep stage or force applied to a subject's teeth, including combinations thereof. For example, monitoring physiological information from the subject can include receiving one or more physiological inputs from the subject during the test period and detecting one or more respiratory events during the test period using the one or more physiological inputs. Detection of respiratory events is discussed in detail above. For example, detecting a respiratory event includes defining and measuring physiological information from a subject against predetermined criteria. A respiratory event is more than mere evidence of obstruction (e.g., a change in respiratory airflow, oxygen saturation, snoring sound, etc.). The one or more respiratory events discussed herein can be an apnea, a hypopnea, a flow limited breath, a snoring event, etc.

As discussed herein, a history of movement includes information associated with a position and/or orientation of a titration device during a titration. The titration device can be the adjustable mandibular displacement device 10 discussed above with regard to FIG. 1A, for example. In other words, the history of movement includes information associated with a position and/or orientation (including a plurality of positions and/or orientations) at one or more discrete times during the titration. Time can optionally be measured in seconds, minutes, hours, or any fraction thereof. The position and/or orientation of the mandibular displacement device can be measured as an amount of protrusion in the anterior-posterior direction, an amount of occlusal separation in the cranial-caudal direction and/or an amount of bite opening. Thus, the information can include position and/or orientation of the titration device as a function of time during the titration. The information can also include a total amount of time the titration device spends at, greater than or less than each of a plurality of positions and/or orientations. Further, the information can include a rate of movement of the titration device between positions and/orientations.

Additionally, when evaluating an outcome of oral appliance therapy based on a comprehensive data set, changes in a protrusion level of the adjustable mandibular displacement device can be monitored during the test period. For example, changes in the protrusion level can be monitored and/or stored using the mandibular displacement device controller 40 and/or the computing device 50 discussed above with regard to FIG. 1B. The changes in the protrusion level of the adjustable mandibular displacement device can define the history of movement of the adjustable mandibular displacement device. Optionally, the history of movement of the adjustable mandibular displacement device can include movement between at least two protrusion levels. Additionally, the history of movement can include an amount of time the adjustable mandibular displacement device spends at each of the at least two protrusion levels.

Optionally, a frequency of respiratory events (e.g., respiratory events/unit time) can be calculated. Detection of respiratory events is discussed in detail above. For example, detecting a respiratory event includes defining and measuring physiological information from a subject against predetermined criteria. It should be understood that during a titration (e.g., in real-time), the frequency of respiratory events can be calculated as the number of respiratory events occurring per unit time. Additionally, it should also be understood that it is possible to calculate a frequency of respiratory events that occurred at a plurality of protrusion levels at a later time using a data set collected during the titration. For example, a number of respiratory events at or above (i.e., at or greater than) each of the plurality of protrusion levels can be determined. Each of the number of respiratory events can then be divided by an amount of time at or above each of the plurality of protrusion levels. This frequency can define a Residual Respiratory Disturbance Index ("Residual RDI"). The Residual RDI is shown below in Eqn. (1).

$$\text{Residual } RDI\ (i) = \frac{\text{\# Respiratory Events at or above Protrusion Level } (i)}{\text{Amount of Time at or above Protrusion Level } (i)}, \quad (1)$$

where i is a discrete protrusion level of the adjustable mandibular displacement device. Optionally, the Residual RDI can be calculated at a plurality of protrusion levels where an amount of time at or above each of the plurality of protrusion levels is at least 5 minutes. In other words, the Residual RDI may optionally not be calculated at protrusion levels where the adjustable mandibular displacement device does not spend a significant amount of time at or above the protrusion level.

Optionally, the history of movement can be analyzed to determine a percentage of time the adjustable mandibular displacement device spends at or below (i.e., at or less than) each of the at least two protrusion levels. For example, the percentage of time at or below each of the protrusion levels can be an amount of time spent at or below each of the plurality of protrusion levels divided by a total amount of time in the test period, which is shown below in Eqn. (2).

$$\% \text{ of Time } (i) = \frac{\text{Amount of Time at or below Protrusion Level } (i)}{\text{Total Amount of Time in the Test Period}}, \quad (2)$$

where i is a discrete protrusion level of the adjustable mandibular displacement device.

Additionally, evaluating an outcome of oral appliance based on a comprehensive data set can include identifying at least one effective protrusion level. For example, evaluating an outcome of oral appliance therapy can include identifying one or more of the plurality of protrusion levels where the frequency of respiratory events is less than the predefined value. Optionally, the frequency of respiratory events can be the Residual RDI discussed above, for example. The predefined value can represent an acceptable frequency of respiratory events per unit time. For example, the predefined value can be an acceptable number of events per hour such as 10 events per hour. The predefined value can be a clinically-acceptable number of events per hour or a subject-specific-acceptable number of events per hour. Thus, it should be understood that the acceptable number of events per hour can be more or less than 10. A protrusion level where the frequency of respiratory events is less than the predefined value can be considered an effective protrusion level for oral appliance therapy because the frequency of respiratory events are reduced to an acceptable level. It should also be understood that a value or range representing a nearly-acceptable number of events per unit time can be established such as 15 or 20 events per hour, for example. Accordingly, a subject can be considered a favorable candidate for oral appliance therapy when the frequency of respiratory events is less than the predefined value. Alternatively, the predefined value can be subject specific. For example, an acceptable number of events per hour can be less than half of the number of events per hour displayed by a subject without therapy, such as would be measured in a baseline study. Additionally, the protrusion level where the frequency of respiratory events is less than the predefined value can be considered the effective protrusion level for oral appliance therapy. On the other hand, a subject can be considered an unfavorable candidate for oral appliance therapy when the frequency of respiratory events is greater than the predefined value for every level of protrusion. The subject can therefore be labeled as a predicted failure when there is no protrusion level where the frequency of respiratory events is less than the predefined value. In addition, a subject can be considered a nearly-favorable candidate for oral appliance therapy when the frequency of respiratory events is less than the value representing a nearly-acceptable frequency of respiratory events. Optionally, a subject can be considered inconclusive when the test period is too short to collect sufficient data and/or the titration device does not spend sufficient time near its upper limit.

Additionally, evaluating an outcome of oral appliance based on a comprehensive data set can include determining whether a percentage of time at or below the at least one effective protrusion level is greater than or equal to a predefined percentage of time. A similar determination can include determining whether a percentage of time at or above the at least one effective protrusion level is less than or equal to a predefined percentage of time. It should be understood that the predefined percentages of time in the cases above would be different but the outcome of the determination would be the same. As discussed above, the history of movement can be analyzed to determine a percentage of time the adjustable mandibular displacement device spends at or below each of a plurality of protrusion levels. A determination can then be made as to whether the percentage of time at or below each of the one or more protrusion levels is greater than or equal to a predefined percentage of the test period. For example, the predefined percentage of the test period can be a majority of the test period. The predefined percentage can be between 75% and 100% such as 85% of the test period, which represents more than a majority of the test period. Accordingly, a subject can optionally be considered a favorable candidate for oral appliance therapy when there is at least one protrusion level for which the frequency of respiratory events is less than the predefined value and the percentage of time is greater than the predefined percentage of time. Additionally, the protrusion level where the frequency of respiratory events is less than the predefined value and the percentage of time is greater than the predefined percentage of time can be considered the effective protrusion level for oral appliance therapy. On the other hand, a subject can optionally be considered an unfavorable candidate for oral appliance therapy when the frequency of respiratory events is greater than the predefined value and/or and the percentage of time is less than the predefined percentage of time.

In addition, it should be understood that there may be more than one protrusion level where the frequency of respiratory events is less than the predefined value. In other words, there can be more than one protrusion level where the frequency of respiratory events are reduced to an acceptable level. In this case, an effective protrusion level for oral appliance therapy can be a smallest protrusion level (e.g., a minimum protrusion level) where the frequency of respiratory events is less than the predefined value and the percentage of time is greater than or equal to the predefined percentage of the test period. Accordingly, the effective protrusion level for oral appliance therapy can be the minimum protrusion level where the frequency of respiratory events are reduced to an acceptable level and where the adjustable mandibular displacement device spends a majority of the test period.

Figure 6A:
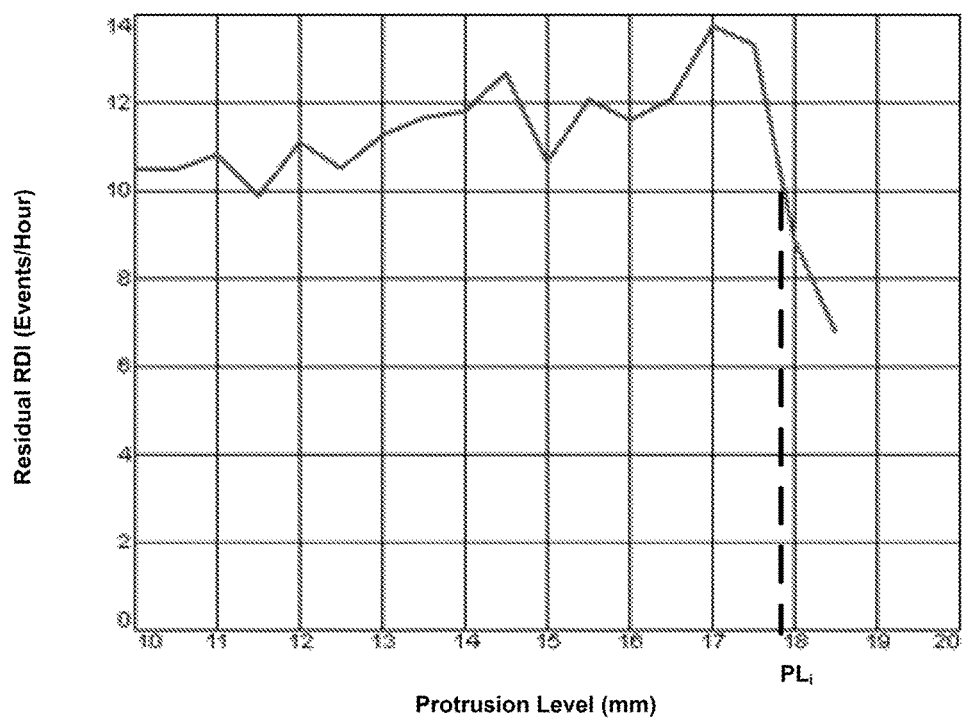
FIG. 6A is a graph illustrating the frequency of respiratory events occurring at or above each of a plurality of protrusion levels.

Optionally, a graphical representation of the frequency of respiratory events at or above each of a plurality of protrusion levels such as the Residual RDI, for example, and/or a graphical representation of the percentage of time at or below each of a plurality of protrusion levels can be generated. Additionally, evaluating an outcome of oral appliance therapy based on a comprehensive data set can be performed using the graphical representation. For example, a determination of whether a subject is a favorable candidate for oral appliance therapy and/or an effective protrusion level can be made using the graphical representation. Referring now to FIG. 6A, a graph illustrating the frequency of respiratory events at or above each of a plurality of protrusion levels is shown. The graph illustrates the Residual RDI (e.g., respiratory events per unit time) versus protrusion level (e.g., mm of protrusion). As shown in FIG. 6A, at approximately $PL_i=17.9$ mm, the Residual RDI is less than 10 respiratory events per hour, which can optionally be the predefined value of events per unit time representing an acceptable frequency of respiratory events, as discussed above. Accordingly, the subject can be considered a favorable candidate for oral appliance therapy because the Residual RDI is less than the predetermined value (e.g., at $PL_i=17.9$ mm). In other words, a protrusion level that reduces occurrence of respiratory events to an acceptable level exists. For example, in FIG. 6A, the effective protrusion level is $PL_i=17.9$ mm. It should be understood that the graph of the Residual RDI versus protrusion level is subject-specific and generated following a titration. Accordingly, the one or more effective protrusion levels are also subject-specific.

Figure 6B:
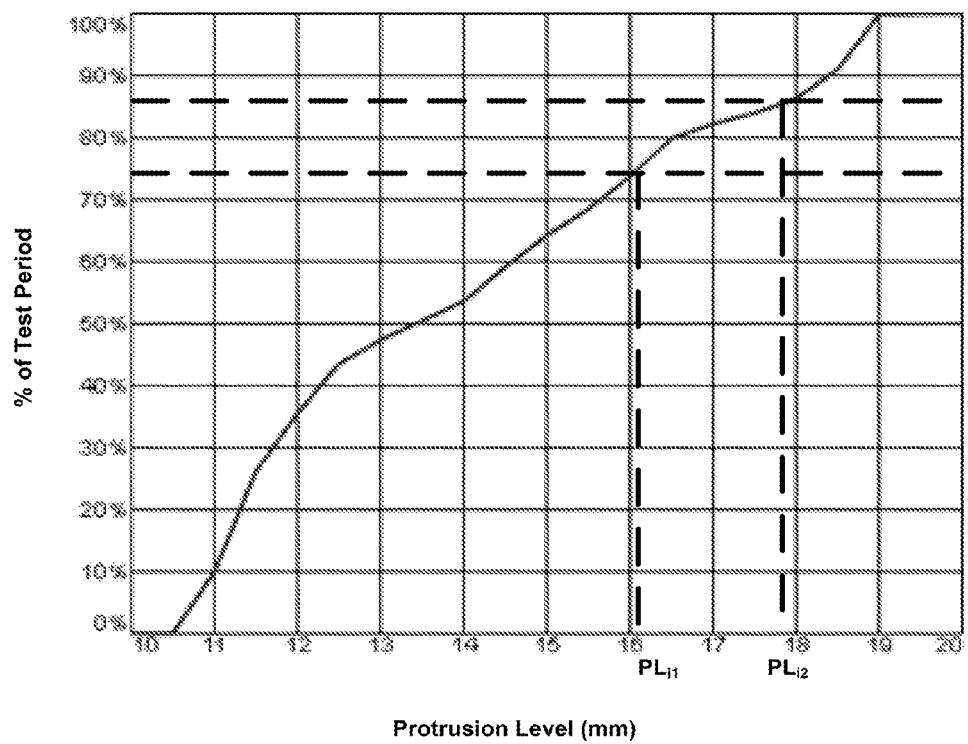
FIG. 6B is a graph illustrating the percentage of time the adjustable mandibular displacement device spends at or below each of a plurality of protrusion levels.

Referring now to FIG. 6B, a graph illustrating the percentage of time at or below each of a plurality of protrusion levels is shown. As discussed above, the subject can be considered a favorable candidate for oral appliance therapy when the frequency of respiratory events (e.g., the Residual RDI) is less than a predefined value (e.g., 10 events per hour, for example) and the percentage of time at or below the given protrusion level is greater than a predetermined percentage of the test period. The predetermined percentage can be a majority of the test period, such as between 75% and 100% of the test period, for example. In FIG. 6B, protrusion levels greater than approximately $PL_{i1}=16.1$ mm represent protrusion levels where the adjustable mandibular displacement device spends greater than 75% of the test period at or below the given protrusion level. Additionally, as shown in FIG. 6B, the adjustable mandibular displacement device spends greater than approximately 87% of the test period at approximately $PL_{i2}=17.9$ mm or less. $PL_{i2}=17.9$ mm also represents the protrusion level where the Residual RDI is less than 10 respiratory events per hour shown in FIG. 6A. Accordingly, the subject can be considered a favorable candidate for oral appliance therapy the Residual RDI is less than the predetermined value (e.g., at $PL_{i2}=17.9$ mm) and the percentage of time at or below $PL_{i2}=17.9$ mm is greater than the predefined percentage of time. In other words, a protrusion level that reduces occurrence of respiratory events to an acceptable level exists. For example, in FIGS. 6A-6B, the effective protrusion level is $PL_{i2}=17.9$ mm. It should be understood that the graph of the percentage of time is subject-specific and generated following a titration. Accordingly, the percentage of time is also subject-specific.

When evaluating an outcome of oral appliance therapy based on a comprehensive data set, a protrusion level of the adjustable mandibular displacement device can be dynamically and automatically controlled during the test period according to any of the methods discussed herein. For example, a protrusion level of the adjustable mandibular displacement device during the test period can be controlled by increasing protrusion level or decreasing protrusion level of the adjustable mandibular displacement device. The protrusion level can be adjusted to reduce or eliminate occurrence of respiratory events to an acceptable level, for example. Alternatively or additionally, a protrusion level of the adjustable mandibular displacement device during the test period can be controlled by adjusting the protrusion level of the adjustable mandibular displacement device based on at least one of frequency or severity of the one or more respiratory events. At least one of a magnitude or rate of adjustment can optionally be related to at least one of frequency or severity of the one or more respiratory events. For example, a greater magnitude and/or rate of adjustment of the protrusion level of the adjustable mandibular displacement device can correspond to a more frequent or severe respiratory event, and a lesser magnitude and/or rate of adjustment of the protrusion level of the adjustable mandibular displacement device can correspond to a less frequent or severe respiratory event. Optionally, a protrusion level of the adjustable mandibular displacement device during the test period can be controlled in response to not detecting a respiratory event during a fixed period of time in order to induce a respiratory event or to induce a change in respiratory airflow. Alternatively or additionally, a protrusion level of the adjustable mandibular displacement device can be controlled during the test period to optimize respiratory airflow.

Figure 5B:
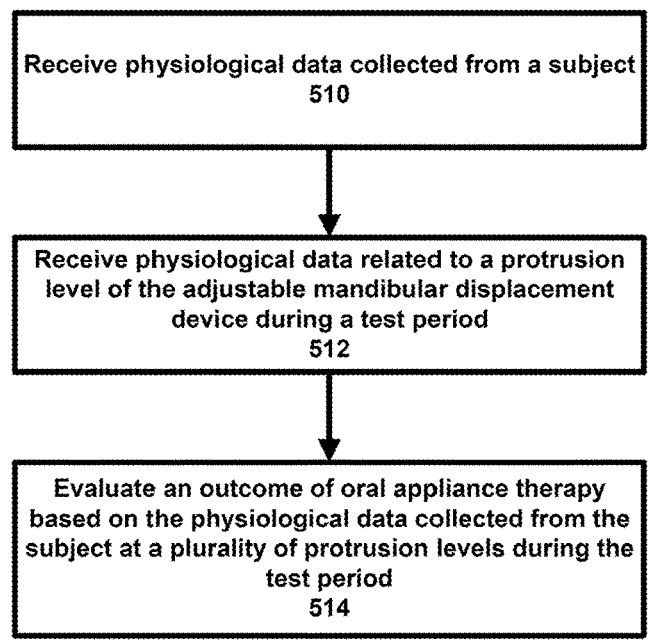
FIG. 5B is a flow diagram illustrating example operations for performing a titration for oral appliance therapy using data collected at a plurality of protrusion levels.

Referring now to FIG. 5B, a flow diagram illustrating example operations 500B for performing a titration for oral appliance therapy using data collected at a plurality of protrusion levels of an adjustable mandibular displacement device. Similarly to above, by evaluating an outcome of oral appliance therapy using data collected a plurality of protrusion levels, the overall response at various protrusion levels during a test period is examined in order to evaluate therapeutic outcome. For example, as discussed below, respiratory events are detected, and in some cases even evoked, and classified. Then, the protrusion level of the titration device is dynamically controlled in response to the respiratory events. The protrusion level can be controlled using a graded dynamic adjustment (e.g., magnitude and rate) according to the classified respiratory events. Therapeutic outcome can then be evaluated based on the overall data set, which includes, but is not limited to, the physiological response of the subject and information regarding the dynamic response of the titration device (e.g., how fast and how far the titration device moves during the test period).

For example, at 510, physiological data (e.g., the physiological information discussed herein) can be received from a subject. Additionally, at 512, data related to a protrusion level of the adjustable mandibular displacement device during the test period can be received. Then, at 514, an outcome of oral appliance therapy can be evaluated based on the physiological data collected from the subject at the plurality of protrusion levels of the adjustable mandibular displacement device during the test period. In the evaluation, the physiological data from the plurality of protrusion levels can be combined (for example, if needed to increase the amount of data to a minimum amount of time, for example greater than 1 hour).

Titrating in a Non-Clinical Setting

Figure 7:
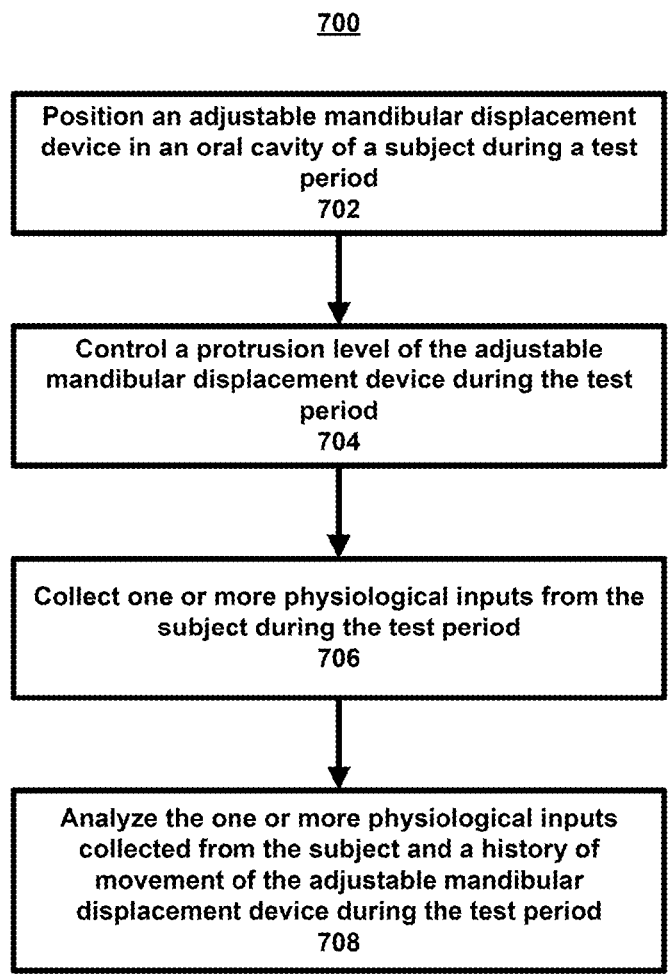
FIG. 7 is a flow diagram illustrating example operations for performing a titration for oral appliance therapy in a non-clinical setting.

Referring now to FIG. 7, a flow diagram illustrating example operations 700 for performing a titration for oral appliance therapy in a non-clinical setting is shown. As discussed herein, a titration in the non-clinical setting can be performed with limited information as compared to traditional sleep testing. In particular, it is possible to perform the titration (e.g., evaluate therapeutic outcome, predict effective protrusion level, etc.) without information collected during a traditional polysomnographic study, for example. The non-clinical setting can be a sleep session occurring outside of a sleep clinic. For example, the non-clinical setting can be a sleep session occurring in the subject's home. Alternatively or additionally, the non-clinical setting can be a sleep session occurring without a polysomnographic technician monitoring the subject and/or without conducting a polysomnographic study. Alternatively or additionally, the non-clinical setting can be a sleep session occurring with a pharmaceutical sleep aid to induce sleep in an office or outpatient setting, including a surgical arena. Optionally, the favorable candidate can be identified regardless of a sleep stage during the test period, a body position during the test period or a worst case scenario (e.g., a period of REM sleep in a supine position).

At 702, an adjustable mandibular displacement device can be positioned in an oral cavity of a subject during a test period. At 704, a protrusion level of the adjustable mandibular displacement device can be controlled during the test period. The protrusion level can be controlled by moving the adjustable mandibular displacement device between at least two protrusion levels, for example. The methods for controlling the adjustable mandibular displacement device can include any of the methods of adjustment discussed herein including, but not limited to, increasing/decreasing protrusion level to reduce/eliminate respiratory events, controlling magnitude or rate of adjustment based on frequency and severity of respiratory events, optimizing airflow, etc. At 706, one or more physiological inputs from the subject during the test period can be collected. In addition, at 708, the one or more physiological inputs collected from the subject and a history of movement of the adjustable mandibular displacement device during the test period can be analyzed. As discussed above, a determination as to whether the subject is a favorable candidate for oral appliance therapy and/or an effective protrusion level of the adjustable mandibular displacement device can be determined by analyzing the one or more physiological inputs collected from the subject and a history of movement of the adjustable mandibular displacement device during the test period.

In the non-clinical setting, the monitored physiological information can include respiratory airflow and oxygen saturation. Optionally, in the non-clinical setting, the monitored physiological information can only include respiratory airflow and oxygen saturation. Accordingly, the physiological inputs can include respiratory airflow and oxygen saturation and exclude other information collected during a polysomnographic study, for example. Respiratory airflow and oxygen saturation can be received from the subject during the test period, and one or more respiratory events can be detected during the test period using the received respiratory airflow and oxygen saturation. Respiratory event detection is discussed in detail above. For example, a respiratory event can be measured and defined according to predetermined criteria.

In the non-clinical setting, predicting whether the subject is a favorable candidate for oral appliance therapy can further include determining a frequency of respiratory events at or above each protrusion level during the test period. For example, the Residual RDI discussed above can be calculated using Eqn. (1). Alternatively or additionally, predicting whether the subject is a favorable candidate for oral appliance therapy can further include determining a percentage of time at or below each protrusion level during the test period. The percentage of time at or below each protrusion level can be calculated using Eqn. (2), for example. As discussed above, the subject can be a favorable candidate when the frequency of respiratory events is less than a predefined value or the percentage of time is greater than a predefined percentage of the test period. Optionally, the subject can be a favorable candidate when the frequency of respiratory events is less than the predefined value and the percentage of time is greater than the predefined percentage. Additionally, as discussed above, an effective protrusion level for oral appliance therapy can be a smallest protrusion level where the frequency of respiratory events is less than the predefined value and the percentage of time is greater than or equal to the predefined percentage.

Automatic Control of a Titration Device During a Titration

Figure 8:
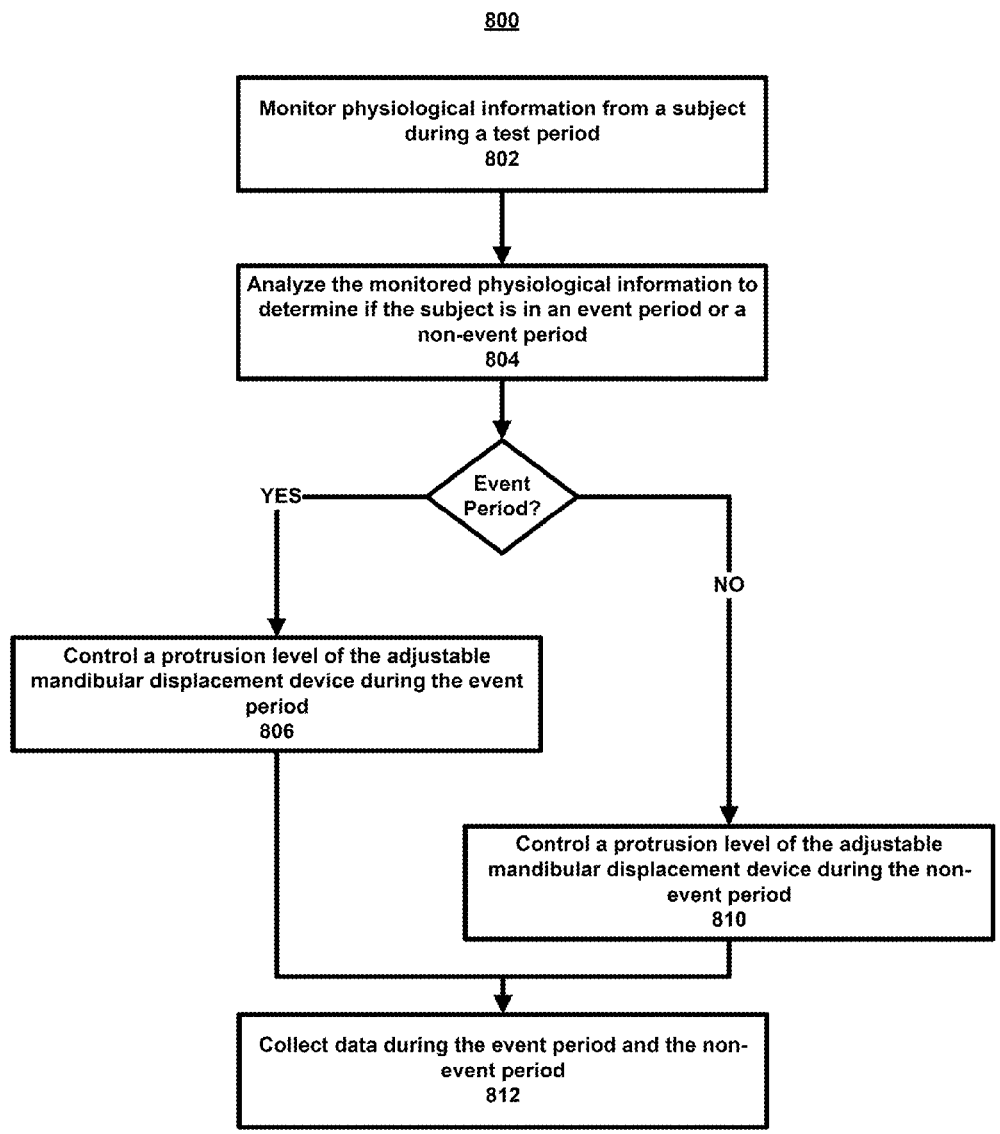
FIG. 8 is a flow diagram illustrating example operations for automatically controlling an adjustable mandibular displacement device while performing a titration for oral appliance therapy.

Referring now to FIG. 8, a flow diagram illustrating example operations 800 for automatically controlling an adjustable mandibular displacement device while titrating for oral appliance therapy is shown. Automatically controlling the adjustable mandibular displacement device can include a plurality of modes (e.g., an event mode and a non-event mode), and adaptive control algorithms can differ in each of the plurality of modes. In the event mode, an object of the adaptive control algorithm can be to adjust the titration device in response to respiratory events. In the non-event mode, an object of the adaptive control algorithm can be to induce respiratory events or a change in respiratory airflow and/or optimize respiratory airflow or to monitor and optimize other physiological inputs such as snoring.

For example, at 802, physiological information from a subject can be monitored during a test period. The test period can include at least one event period and at least one non-event period. At 804, the monitored physiological information can be analyzed to determine if the subject is in the at least one event period or the at least one non-event period. At 806, a protrusion level of the adjustable mandibular displacement device can be controlled during the at least one event period. At 808, a protrusion level of the adjustable mandibular displacement device can be controlled during the at least one non-event period. As discussed above, adaptive control algorithms are different for the event period and the non-event period. At 810, data can be collected during the at least one event period and the at least one non-event period.

An event period includes a portion of the test period where a frequency of the one or more respiratory events is greater than a predetermined threshold. Additionally, a non-event period includes a portion of the test period wherein a frequency of the one or more respiratory events is less than a predetermined threshold. For example, the predetermined threshold can be selected with the objectives discussed above in mind. In the event mode, the object can be to respond to respiratory events. When adjusting protrusion level in response to respiratory events, protrusion level can be increased to a point at which respiratory events are reduced or eliminated to an acceptable level (e.g., the frequency of respiratory event occurrence decreases). After respiratory events are reduced or eliminated below an acceptable level, and fewer respiratory events are occurring such that the protrusion level is not being adjusted as frequently in response to respiratory events, the adjustable mandibular displacement device can be controlled to induce respiratory events or a change in respiratory airflow or to optimize airflow, for example.

Optionally, collecting data can include collecting data regarding a history of movement of the adjustable mandibular displacement device during the at least one event period and the at least one non-event period. Alternatively or additionally, analyzing the monitored physiological information can include detecting one or more respiratory events. Respiratory event detection is discussed in detail above.

Additionally, during the event period, controlling a protrusion level of the adjustable mandibular displacement device can include at least one of increasing the protrusion level or decreasing the protrusion level of the adjustable mandibular displacement device. Optionally, controlling a protrusion level of the adjustable mandibular displacement device during the at least one event period can include adjusting the protrusion level of the adjustable mandibular displacement device based on at least one of frequency or severity of the one or more respiratory events. As discussed above, at least one of a magnitude and rate of adjustment can be related to at least one of frequency or severity of the one or more respiratory events.

Alternatively or additionally, during the non-event period, controlling the protrusion level of the adjustable mandibular displacement device can include adjusting the protrusion level to induce a change in respiratory airflow. For example, the protrusion level can be decreased to induce a respiratory event. In addition, the protrusion level of the adjustable mandibular displacement device can be controlled to optimize respiratory airflow. Methods for optimizing respiratory airflow are discussed in detail above.

Alternatively or additionally, during the non-event period, controlling the protrusion level of the adjustable mandibular displacement device can include adjusting the protrusion level to monitor changes in snoring. For example, the protrusion level can be adjusted to test or optimize the protrusive level such that amount, magnitude or degree of snoring is minimized while maintaining events below a predetermined threshold.

Titrating Based on Attractor Behavior

As discussed herein, attractor behavior occurs at a protrusion level where a small increase in the protrusion level results in an insignificant change in respiratory airflow (e.g., peak ventilation) and a small decrease in the protrusion level results in a signification change in respiratory airflow (e.g., peak ventilation). Attractor behavior can be discovered while controlling the protrusion level to optimize respiratory airflow (e.g., during the search for $P_{opt}/P_{crit}$) which is discussed above. Observance of attractor behavior can occur after the respiratory events have been eliminated, but it is not required. For instance the attractor behavior can be observed at a protrusive level where the respiratory event frequency is not below a predetermined threshold at the time of detection. It should be understood that the mechanics of the pharynx provide this particularly sensitive spot. Additionally, while a more gradual form of attractor behavior is observed during CPAP therapy, attractor behavior during OA therapy is more severe and abrupt. Accordingly, the protrusion level at which attractor behavior occurs can be the effective protrusion level for oral appliance therapy.

Figure 9:
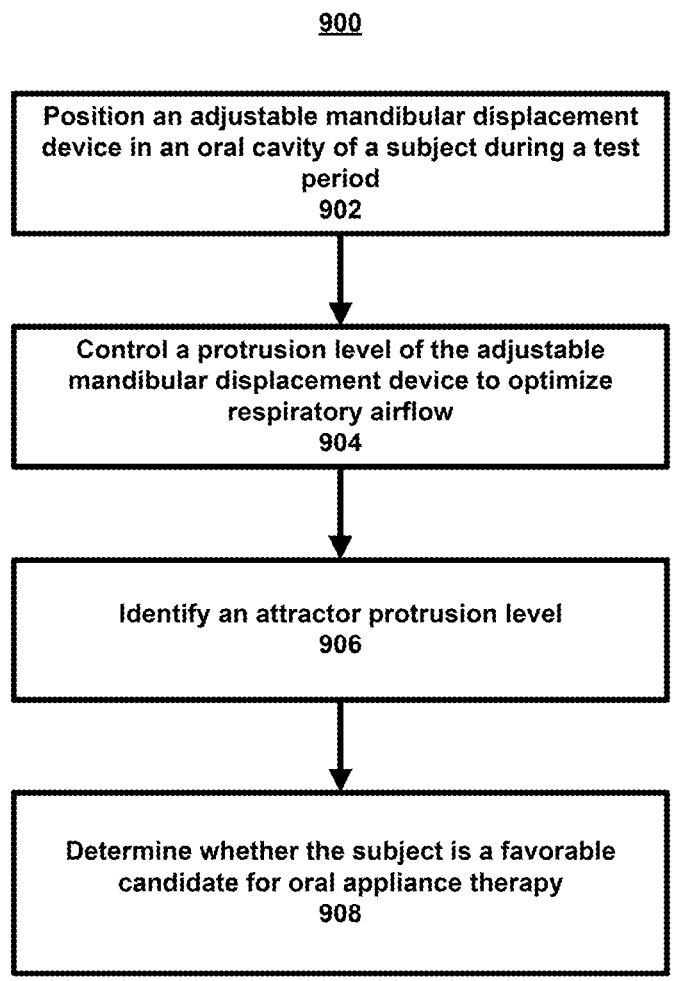
FIG. 9 is a flow diagram illustrating example operations for identifying a candidate for oral appliance therapy based on attractor behavior.

Referring now to FIG. 9, a flow diagram illustrating example operations 900 for identifying a candidate for oral appliance therapy based on attractor behavior is shown. At 902, an adjustable mandibular displacement device can be positioned in an oral cavity of a subject during a test period. At 904, the protrusion level of the adjustable mandibular displacement device can be controlled to optimize respiratory airflow. Methods for optimizing airflow are discussed in detail above. For example, the protrusion level can be controlled in a search for $P_{opt}/P_{crit}$. At 906, an attractor protrusion level can be identified. The attractor protrusion level is a protrusion level where a small increase in the protrusion level results in an insignificant change in respiratory airflow and a small decrease in the protrusion level results in a signification change in respiratory airflow. When identifying attractor behavior, a perturbation (e.g., a small change in protrusion level) is made, and the effect on respiratory airflow is immediately examined (e.g., within a predetermined time from the change in protrusion level) to observe the mechanical effect on the airway. For instance within 5 breaths, or approximately 20 seconds. After this time, chemo reflexes take over and attractor behavior fades. At 908, in response to identifying an attractor protrusion level, a determination can be made that the subject is a favorable candidate for oral appliance therapy. Optionally, an effective protrusion level for oral appliance therapy can be approximately the attractor protrusion level. Additionally, in response to not identifying an attractor protrusion level, a titration can be performed based on a history of movement of the adjustable mandibular displacement device and one or more respiratory events during the test period.

Multi-Test-Period Protocol

As discussed herein, a multi-test-period protocol includes performing at least two titrations during separate and distinct test periods (e.g., a first test period and a second test period, for example). Optionally, the second test period can be subsequent to the first test period. For example, the first test period can be sleep during a first session, and the second test period can be sleep during a second session. Optionally, the first test period can be sleep during a first night, and the second test period can be sleep during a second night. Optionally, the first test period can be sleep during a first portion of the night, and the second test period can be sleep during a second portion of the same night. The test protocol in the first period can be the same or different than the test protocol in the second test period. Alternatively or additionally, the first test period can include sleep in one of a supine or lateral position, and the second test period can include sleep in the other of the supine or lateral position. Optionally, the second test period can include sleep with a different therapeutic intervention than the first test period. For example, the therapeutic intervention during the first test period and the second test period can be at least one of an oral appliance, a different amount of occlusal separation or an oral appliance used in conjunction with CPAP.

Figure 10A:
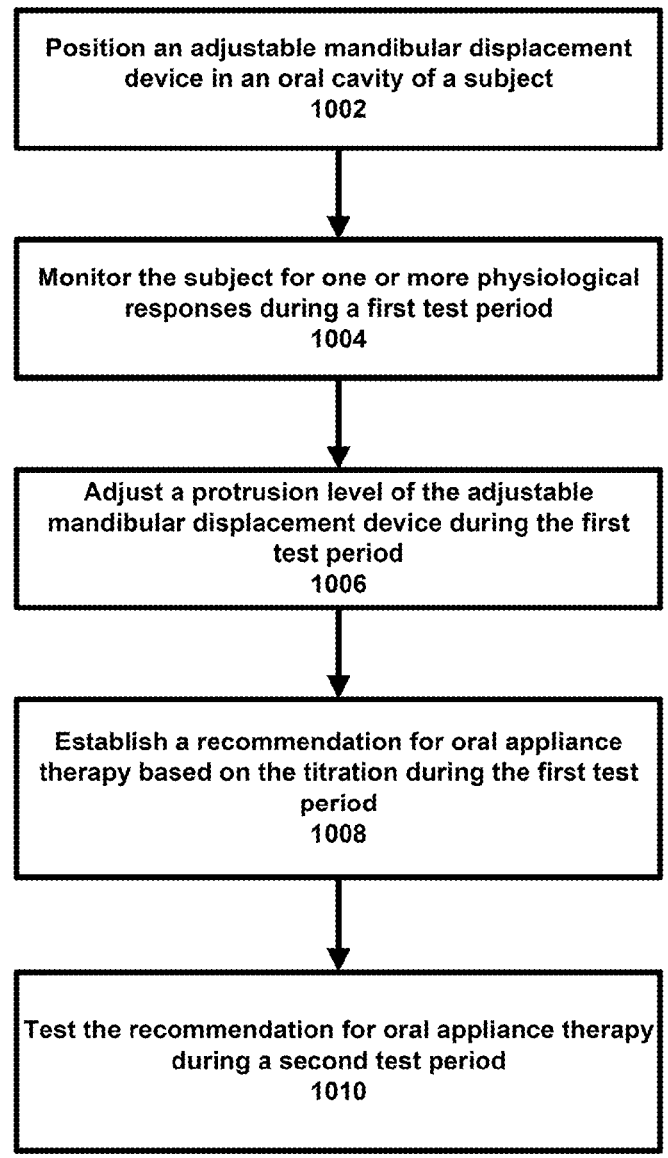
FIGS. 10A-10C are a flow diagrams illustrating example operations for performing a titration for oral appliance therapy using a multi-test-period protocol.

Referring now to FIG. 10A, a flow diagram illustrating example operations 1000A for performing a titration for oral appliance therapy using a multi-test-period protocol is shown. At 1002, an adjustable mandibular displacement device can be positioned in an oral cavity of a subject. At 1004, the subject can be monitored for one or more physiological responses during a first test period. Optionally, a physiological response can be a respiratory event, for example. Detecting respiratory events is discussed in detail above. For example, detecting a respiratory event includes defining and measuring physiological information from a subject against predetermined criteria. At 1006, a protrusion level of the adjustable mandibular displacement device can be adjusted during the first test period. Methods for controlling the adjustable mandibular displacement device are discussed above including, but not limited to, increasing/decreasing a protrusion level, controlling a protrusion level based on frequency or severity of respiratory events, optimizing respiratory airflow, etc. At 1008, a recommendation for oral appliance therapy can be established based on the titration of the protrusion level of the adjustable mandibular displacement device during the first test period. The recommendation can be whether the subject is a predicted success (e.g., a favorable candidate for oral appliance therapy), an effective protrusion level or a range of effective protrusion levels, etc. Then, at 1010, the recommendation for oral appliance therapy can be tested and/or refined during a second test period.

Additionally, testing the recommendation for oral appliance therapy can include monitoring the subject for one or more physiological responses during the second test period. The recommendation for oral appliance therapy can be confirmed, refined or rejected based on the one or more physiological responses during the second test period. For example, if the outcomes of the titration during the first and second test periods are consistent, the recommendation can be confirmed. However, if the outcomes of the titration during the first and second test periods are inconsistent, the recommendation can be rejected. If the recommendation is rejected, a third test period may be used to confirm the new recommendation or to provide or refine a target protrusive position if the recommendation was altered from predicted failure to predicted success. It should be understood that the outcomes can be whether the subject is a predicted success (e.g., a favorable candidate for oral appliance therapy), an effective protrusion level or a range of effective protrusion levels, etc.

In addition, establishing a recommendation for oral appliance therapy can include identifying a range of effective protrusion levels for oral appliance therapy. For example, the range of effective protrusion levels can be between x and y mm, for example. Optionally, testing the recommendation for oral appliance therapy can include adjusting the protrusion level of the adjustable mandibular displacement device within the range of effective protrusion levels during the second test period. In other words, during the second test period, the adjustable mandibular displacement device is adjusted within the range of effective protrusion levels (e.g., between x and y mm, for example). Optionally, an effective protrusion level for oral appliance therapy can be identified based on the adjustment of the protrusion level of the adjustable mandibular displacement device during the second test period. Accordingly, a rough estimate or range of effective protrusion levels is identified during the first test period, and the effective protrusion level is refined during the second test period.

Alternatively or additionally, establishing a recommendation for oral appliance therapy can include identifying an effective protrusion level for oral appliance therapy during the first test period. In addition, testing the recommendation for oral appliance therapy can include fixing the adjustable mandibular displacement device at the effective protrusion level during the second test period. When the adjustable mandibular displacement device is fixed, it is not or minimally adjusted during the second test period. Instead, the subject is monitored for physiological responses during the second test period at the recommended effective protrusion level for confirmatory purposes.

Optionally, a measure of predicted therapeutic outcome for oral appliance therapy can be provided. For example, the measure of predicted therapeutic outcome can be at least one of an Apnea-Hypopnea Index, a Mean $O_2$ Saturation, and Inspiratory Flow Limitation Index or a Respiratory Disturbance Index.

Figure 10B:
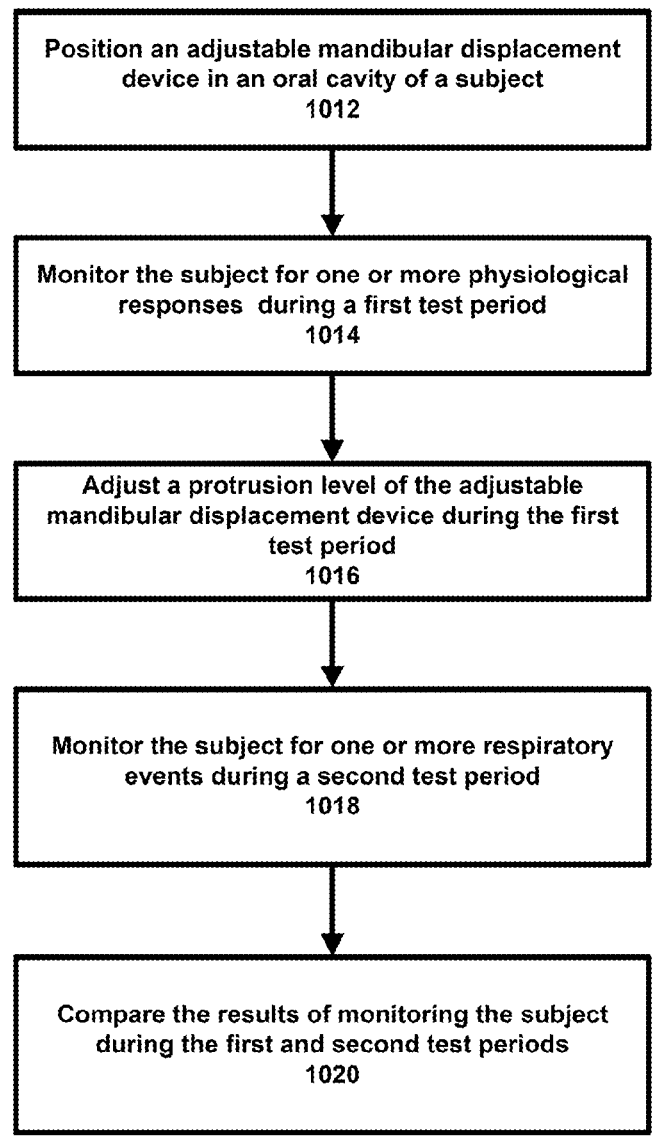

Referring now to FIG. 10B, a flow diagram illustrating example operations 1000B for titrating for oral appliance therapy using a multi-test-period protocol is shown. At 1012, an adjustable mandibular displacement device can be positioned in an oral cavity of a subject. At 1014, the subject can be monitored for one or more physiological responses during a first test period. Optionally, a physiological response can be a respiratory event, for example. Detecting respiratory events is discussed in detail above. For example, detecting a respiratory event includes defining and measuring physiological information from a subject against predetermined criteria. At 1016, a protrusion level of the adjustable mandibular displacement device can be adjusted during the first test period. Methods for controlling the adjustable mandibular displacement device are discussed above including, but not limited to, increasing/decreasing a protrusion level, controlling a protrusion level based on frequency or severity of respiratory events, optimizing respiratory airflow, etc. At 1018, the subject can be monitored for one or more physiological responses during a second test period. Then, at 1020, the results of monitoring the subject for one or more physiological responses during the first test period can be compared with results of monitoring the subject for one or more physiological responses during the second test period.

Optionally, the protrusion level of the adjustable mandibular displacement device can be adjusted during the second test period. Methods for controlling the adjustable mandibular displacement device are discussed above including, but not limited to, increasing/decreasing a protrusion level, controlling a protrusion level based on frequency or severity of respiratory events, optimizing respiratory airflow, etc. Alternatively or additionally, a recommendation for oral appliance therapy can be established based on the adjustment of the protrusion level of the adjustable mandibular displacement device during the first test period, and the recommendation for oral appliance therapy can be confirmed, refined or rejected based on the based on the adjustment of the protrusion level of the adjustable mandibular displacement device during the second test period.

Figure 10C:
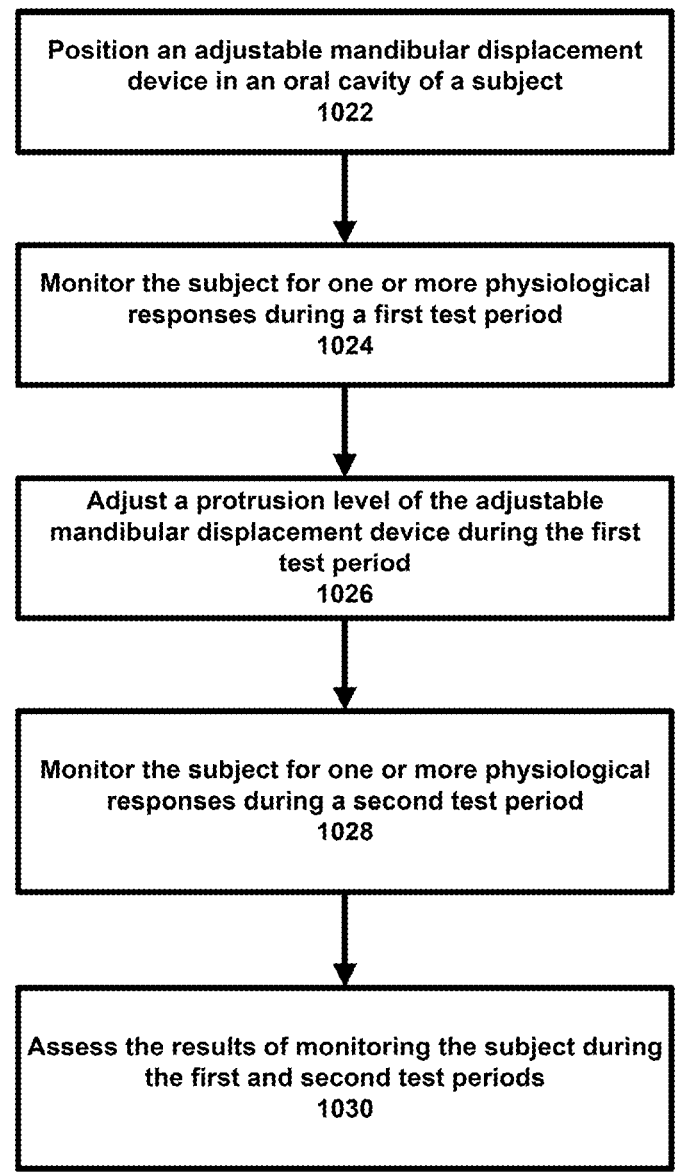

Referring now to FIG. 10C, a flow diagram illustrating example operations 1000C for a multi-test-period protocol for titrating for oral appliance therapy is shown. At 1022, an adjustable mandibular displacement device can be positioned in an oral cavity of a subject. At 1024, the subject can be monitored for one or more physiological responses during a first test period. Optionally, a physiological response can be a respiratory event, for example. Detecting respiratory events is discussed in detail above. For example, detecting a respiratory event includes defining and measuring physiological information from a subject against predetermined criteria. At 1026, a protrusion level of the adjustable mandibular displacement device can be adjusted during the first test period. Methods for controlling the adjustable mandibular displacement device are discussed above including, but not limited to, increasing/decreasing a protrusion level, controlling a protrusion level based on frequency or severity of respiratory events, optimizing respiratory airflow, etc. At 1028, the subject can be monitored for one or more physiological responses during a second test period. Then, at 1020, results of monitoring the subject for one or more physiological responses during the first test period and results of monitoring the subject for one or more physiological responses during the second test period can be assessed.

For example, assessing results of monitoring the subject for one or more physiological responses during the first test period and results of monitoring the subject for one or more physiological responses during the second test period can include averaging or combining the results of monitoring the subject for one or more physiological responses during the first test period and the results of monitoring the subject for one or more physiological responses during the second test period. The method can further include establishing a recommendation for oral appliance therapy based on the assessed results.

Example Computing Device

It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 11:
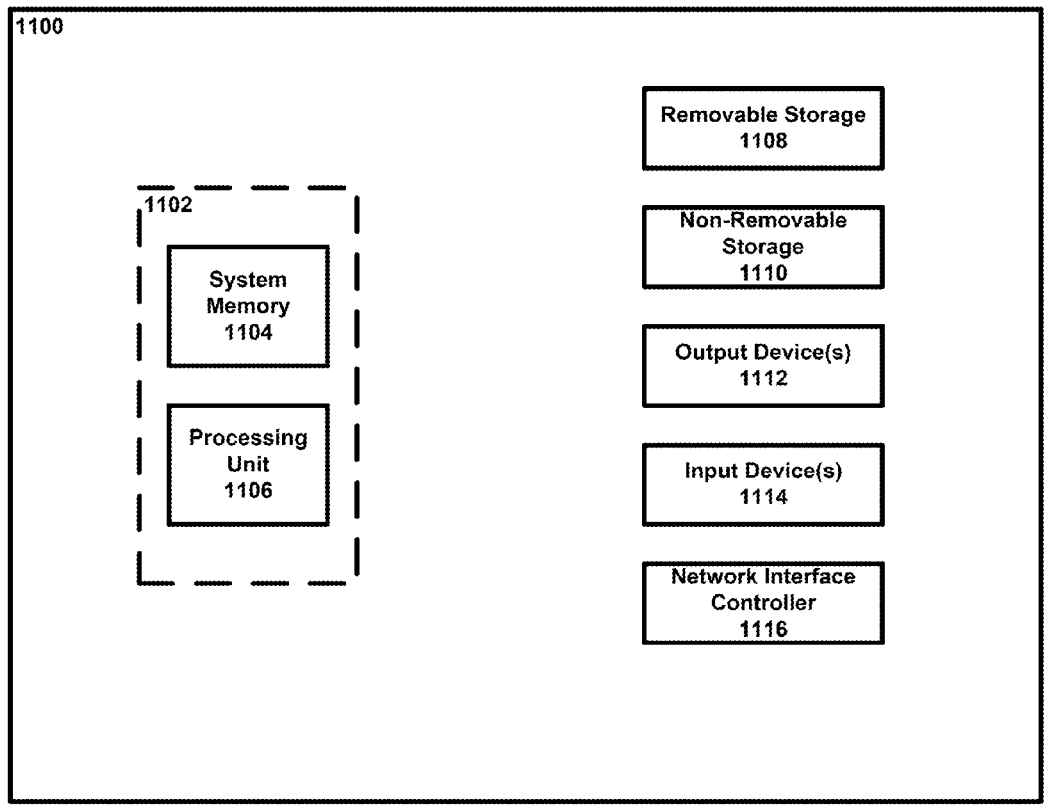
FIG. 11 is a block diagram of an example computing device.

When the logical operations described herein are implemented in software, the process may execute on any type of computing architecture or platform. For example, referring to FIG. 11, an example computing device upon which embodiments of the invention may be implemented is illustrated. For example, the mandibular displacement device controller 40 and/or the computing device 50 discussed with regard to FIG. 1 can be implemented as computing device 1100. The computing device 1100 may include a bus or other communication mechanism for communicating information among various components of the computing device 1100. In its most basic configuration, computing device 1100 typically includes at least one processing unit 1106 and system memory 1104. Depending on the exact configuration and type of computing device, system memory 1104 may be volatile (such as random access memory (RAM)), non-volatile (such as read-only memory (ROM), flash memory, etc.), or some combination of the two. This most basic configuration is illustrated in FIG. 11 by dashed line 1102. The processing unit 1106 may be a standard programmable processor that performs arithmetic and logic operations necessary for operation of the computing device 1100.

Computing device 1100 may have additional features/functionality. For example, computing device 1100 may include additional storage such as removable storage 1108 and non-removable storage 1110 including, but not limited to, magnetic or optical disks or tapes. Computing device 1100 may also contain network connection(s) 1116 that allow the device to communicate with other devices. Computing device 1100 may also have input device(s) 1114 such as a keyboard, mouse, touch screen, etc. Output device(s) 1112 such as a display, speakers, printer, etc. may also be included. The additional devices may be connected to the bus in order to facilitate communication of data among the components of the computing device 1100. All these devices are well known in the art and need not be discussed at length here.

The processing unit 1106 may be configured to execute program code encoded in tangible, computer-readable media. Computer-readable media refers to any media that is capable of providing data that causes the computing device 1100 (i.e., a machine) to operate in a particular fashion. Various computer-readable media may be utilized to provide instructions to the processing unit 1106 for execution. Common forms of computer-readable media include, for example, magnetic media, optical media, physical media, memory chips or cartridges, a carrier wave, or any other medium from which a computer can read. Example computer-readable media may include, but is not limited to, volatile media, non-volatile media and transmission media. Volatile and non-volatile media may be implemented in any method or technology for storage of information such as computer readable instructions, data structures, program modules or other data and common forms are discussed in detail below. Transmission media may include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 1106 may execute program code stored in the system memory 1104. For example, the bus may carry data to the system memory 1104, from which the processing unit 1106 receives and executes instructions. The data received by the system memory 1104 may optionally be stored on the removable storage 1108 or the non-removable storage 1110 before or after execution by the processing unit 1106.

Computing device 1100 typically includes a variety of computer-readable media. Computer-readable media can be any available media that can be accessed by device 1100 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 1104, removable storage 1108, and non-removable storage 1110 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 1100. Any such computer storage media may be part of computing device 1100.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

EXAMPLE 1

A study to test the efficacy of an automated titration study was performed in the sleep clinic under the supervision of a technician.

Fourteen subjects were recruited and subjected to an overnight titration test at a sleep centre with the automated RCMP device. Each subject had previously received a two night baseline, pre-treatment, respiratory evaluation in the home using a portable sleep monitor. Each subject was then evaluated by the dental co-investigator and fitted with upper and lower dental titration trays filled with the impression material. The dentist measured the maximum retrusion and protrusion values from the scale on the titration trays.

On the night of the automated titration study, a trained polysomnography technician entered the same values of retrusion and protrusion into the RCMP titration software. The titration trays were attached to the mandibular positioner and the position of the trays was adjusted by the manually adjustable knob to near full retrusion. The trays were then inserted into the subject's mouth and used for the duration of the titration study. Once the patient was asleep, the RCMP device was controlled with a decision making algorithm (e.g., in accordance with the implementations for conducting a titration for oral appliance therapy discussed above). The algorithm continuously receives feedback information (e.g., SaO2—oxygen saturation and naris specific air flow), automatically detects and classifies apneas and hypopneas, and makes moment-to-moment decisions regarding mandibular positioning.

The collected data was analyzed to identify if the residual RDI was below a threshold value of 10 events per hour at a protrusive level where the mandibular positioner spent at least 85% of the night at or above this level. Based on this analysis the subjects were predicted to be either a successful or unsuccessful candidate for oral appliance therapy, and a target protrusive position was determined.

The same fourteen patients had been previously studied with the manual RCMP. From the manual RCMP study, the subjects had been previously fitted with a permanent mandibular repositioning appliance (MRA) and tested in a post-treatment, respiratory evaluation during sleep using the same portable monitor used for baseline studies for two nights in the home with the mandibular repositioning appliance (MRA).

The prediction of success and the target protrusive distance from the automated titration study was compared with the therapeutic outcome of the patient as measured in the manual RCMP protocol. For those subjects predicted to be a success, the predicted target protrusive position was compared with the target protrusive position determined in the manual RCMP protocol.

All seven subjects predicted to be a success with the automated titration protocol were found to be a success with the permanent MRA. Five of the seven subjects predicted to be a failure with the automated titration protocol were correctly predicted (i.e., they did not achieve a therapeutic outcome with the permanent MRA) while two subjects that had been predicted to be a failure were incorrectly predicted (i.e., they did achieve a therapeutic outcome with the permanent MRA). Sensitivity was calculated as 78% and specificity was calculated as 100%.

EXAMPLE 2

A study to test the efficacy of an automated titration study was performed unattended, in the home environment.

Fifty-eight subjects were recruited and subjected to a multi-night, in home titration test with the automated RCMP device. Each subject had previously received a two night baseline, pre-treatment, respiratory evaluation in the home using a portable sleep monitor. Each subject was then evaluated by the dental co-investigator and fitted with upper and lower dental titration trays filled with the impression material. The dentist measured the maximum retrusion and protrusion values from the scale on the titration trays.

On the first night of the automated titration study, a clinical coordinator visited the home of the subject to set up the equipment and entered the values of retrusion and protrusion into the RCMP titration software. The titration trays were attached to the mandibular positioner and the position of the trays was adjusted by the manually adjustable knob to near full retrusion. The subject was shown how to place the trays in their mouth and how to wear the finger oximeter and the nasal cannulae. They were provided with a brief tutorial on how to run the software. Before going to sleep, the subject placed the trays into their mouth for the duration of the titration study. Once the patient was asleep, the RCMP device was controlled with a decision making algorithm (e.g., in accordance with the techniques for conducting a titration for oral appliance therapy discussed above). The algorithm continuously receives feedback information (e.g., SaO2—oxygen saturation and naris specific air flow), automatically detects and classifies apneas and hypopneas, and makes moment-to-moment decisions regarding mandibular positioning.

When the night study concluded, the data was automatically uploaded to a central server and accessed by a trained technician who analyzed the data to identify if the residual RDI was below a threshold value of 10 events per hour at a protrusive level where the mandibular positioner spent at least 85% of the night at or above this level. Based on this analysis the subjects were predicted to be either a successful or unsuccessful candidate for oral appliance therapy, and a target protrusive position was determined. If insufficient data was obtained (e.g., less than 4 hours), the night was repeated.

On the second night of the automated titration study, the clinical coordinator returned and set the device to run a confirmation protocol to test the evaluation from the first night. The protocol was set to hold the adjustable appliance at the determined target protrusive position, and would automatically adjust only if respiratory events above a certain threshold were detected. If the subject was predicted to be unsuccessful for oral appliance therapy, the protrusive position was held at a high protrusive position to verify the prediction. When the second night study concluded, the data was automatically uploaded to a central server and accessed by a trained technician who analyzed the data.

If the outcome from the first and second night conflicted, a third night was used to either refine the target protrusive distance or to establish a final prediction. In some cases, an additional night was collected with the appliance set at an increased separation of the occlusal planes (7 mm instead of 3 mm) and the outcome was compared against the evaluation of outcome from the first night of study, to compare both the prediction and the target protrusive distance.

The subject returned to the dentist to be fitted with a permanent mandibular repositioning appliance (MRA) and tested in a post-treatment, respiratory evaluation during sleep using the same portable monitor used for baseline studies for two nights in the home with the mandibular repositioning appliance (MRA).

Of the 45 subjects that were predicted to be a success with oral appliance therapy, 41 achieved a therapeutic AHI of less than 10 per hour and a greater than 50% reduction from baseline. Of the thirteen subjects that were predicted to be a failure with oral appliance therapy, nine were correctly predicted (i.e., they did not achieve a therapeutic outcome with the permanent MRA) while four subjects that had been predicted to be a failure were incorrectly predicted (i.e., they did achieve a therapeutic outcome with the permanent MRA). Sensitivity was calculated as 91% and specificity was calculated as 69%. The target protrusive position was correctly predicted in all 41 of the subjects that achieved a therapeutic outcome.

EXAMPLE 3

A study to test the efficacy of an automated titration study was performed unattended, in the home environment.

In the study described above (Example 2) the collected data was analyzed for occurrences of the attractor behavior. In subjects predicted to be successful with oral appliance therapy were found to have a greater number of instances of attractor behaviour than subjects predicted to be unsuccessful with oral appliance therapy. For example, greater than five per hour instead of less than three per hour.

EXAMPLE 4

A study to demonstrate an automated titration study for high upper airway resistance was performed in sleep clinic under the supervision of a technician.

One subject was recruited and subjected to an overnight titration test at a sleep centre with the automated RCMP device that had been specially modified to include accelerometers to measure body position and a microphone to detect acoustic energy. The subject had previously received a two night baseline, pre-treatment, respiratory evaluation in the home using a portable sleep monitor and had been evaluated by the dental co-investigator and fitted with upper and lower dental titration trays filled with the impression material. The dentist measured the maximum retrusion and protrusion values from the scale on the titration trays.

On the night of the automated titration study, a trained polysomnography technician entered the same values of retrusion and protrusion into the RCMP titration software. The titration trays were attached to the mandibular positioner and were then inserted into the subject's mouth and used for the duration of the titration study. Once the patient was asleep, the RCMP device was controlled with a decision making algorithm (e.g., in accordance with the techniques for conducting a titration for oral appliance therapy discussed above). The algorithm continuously receives feedback information (e.g., SaO2, sound, and naris specific airflow), and uses a trained neural network (e.g., the classifying system) to evaluate, in real time, if each recorded breath is flow limited. The outcome from this evaluation is then used to make moment-to-moment decisions regarding mandibular positioning including a series of protrusive searches in response to higher incidence of inspiratory flow limited breaths.

The collected data was analyzed to determine at what levels protrusive searches were successful at eliminating or minimizing the prevalence of inspiratory flow limited breaths. These were then combined to give an estimate for the optimal protrusive position to treat High Upper Airway Resistance.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A system for performing a titration for oral appliance therapy, comprising:
    an adjustable mandibular displacement device configured to be positioned in an oral cavity of a subject;
    a monitoring unit configured to sense physiological information from the subject during a test period; and
    a control unit comprising a processing unit and a memory operatively coupled to the processing unit, the memory having computer-executable instructions stored thereon that, when executed by the processing unit, cause the system to:
    receive one or more physiological inputs from the monitoring unit during the test period;
    detect one or more respiratory events during the test period using the one or more psychological inputs;
    adjust a protrusion level of the adjustable mandibular displacement device during the test period based on at least one of frequency or severity of the one or more respiratory events, at least one of a magnitude or rate of adjustment being related to at least one of the frequency or the severity of the one or more respiratory events; and
    evaluate an outcome of oral appliance therapy with a mandibular repositioning appliance based on a history of movement of the adjustable mandibular displacement device and the physiological information during the test period.

2. The system of claim 1, wherein the evaluation comprises predicting whether the subject is a favorable candidate for oral appliance therapy or predicting an effective protrusion level of the adjustable mandibular displacement device.

3. The system of claim 2, wherein evaluating an outcome of oral appliance therapy further comprises determining whether a frequency of respiratory events at or above a given protrusion level during the test period is less than a predefined value or determining whether a percentage of time at or below a given protrusion level is greater than or equal to a predefined percentage of the test period.

4. The system of claim 3, wherein the memory has further computer-executable instructions stored thereon that, when executed by the processing unit, cause the system to calculate a frequency of respiratory events at a plurality of protrusion levels by:
    determining a number of respiratory events at or above each of the plurality of protrusion levels; and
    dividing each of the number of respiratory events by an amount of time at or above each of the plurality of protrusion levels, wherein titrating further comprises identifying one or more of the plurality of protrusion levels where the frequency of respiratory events is less than the predefined value.

5. The system of claim 4, wherein evaluating an outcome of oral appliance therapy further comprises determining whether a percentage of time at or below each of the one or more protrusion levels is greater than or equal to a predefined percentage of the test period.

6. The system of claim 5, wherein the memory has further computer-executable instructions stored thereon that, when executed by the processing unit, cause the system to determine that an effective protrusion level for oral appliance therapy is a smallest protrusion level where the frequency of respiratory events at the one or more of the plurality of protrusion levels during the test period is less than the predefined value and the percentage of time at or below the one or more of the plurality of protrusion levels is greater than or equal to the predefined percentage of the test period.

7. The system of claim 3, wherein the memory has further computer-executable instructions stored thereon that, when executed by the processing unit, cause the system to determine that an effective protrusion level for oral appliance therapy is a smallest protrusion level where the frequency of respiratory events at or above the given protrusion level during the test period is less than the predefined value and the percentage of time at or below the given protrusion level is greater than or equal to the predefined percentage of the test period.

8. The system of claim 4, wherein the frequency of respiratory events is calculated at a plurality of protrusion levels where an amount of time at or above each of the plurality of protrusion levels is at least 5 minutes.

9. The system of claim 2, wherein titrating further comprises optimizing the effective protrusion level of the adjustable mandibular displacement device using the one or more physiological inputs from the subject.

10. The system of claim 9, wherein the monitoring unit further comprises a force sensor, and the one or more physiological inputs comprise a force applied on the subject's teeth by the adjustable mandibular displacement device.

11. The system of claim 1, wherein the memory has further computer-executable instructions stored thereon that, when executed by the processing unit, cause the system to monitor changes in a protrusion level of the adjustable mandibular displacement device during the test period, wherein the changes in the protrusion level of the adjustable mandibular displacement device define the history of movement of the adjustable mandibular displacement device.

12. The system of claim 11, wherein the history of movement of the adjustable mandibular displacement device comprises movement between at least two protrusion levels.

13. The system of claim 12, wherein the history of movement includes an amount of time the adjustable mandibular displacement device spends at each of the at least two protrusion levels.

14. The system of claim 13, wherein the memory has further computer-executable instructions stored thereon that, when executed by the processing unit, cause the system to analyze the history of movement to determine a percentage of time the adjustable mandibular displacement device spends at or below each of the at least two protrusion levels.

15. The system of claim 14, wherein the evaluation is based on a frequency of respiratory events at or above each of the at least two protrusion levels and the percentage of time the adjustable mandibular displacement device spends at or below each of the at least two protrusion levels.

16. The system of claim 15, wherein the memory has further computer-executable instructions stored thereon that, when executed by the processing unit, cause the system to generate a graphical representation of at least one of the frequency of respiratory events at or above each of the at least two protrusion levels and the percentage of time the adjustable mandibular displacement device spends at or below each of the at least two protrusion levels, wherein the evaluation is based on the graphical representation.

17. The system of claim 1, wherein the memory has further computer-executable instructions stored thereon that, when executed by the processing unit, cause the system to:
classify a magnitude of severity of at least one of the one or more respiratory events, and wherein adjusting a protrusion level of the adjustable mandibular displacement device during the test period comprises determining at least one of a magnitude and rate of adjustment of the protrusion level based on the magnitude of severity of the respiratory event.

18. The system of claim 17, wherein the monitoring unit further comprises an airflow monitor and an oxygen saturation monitor, and the one or more physiological inputs from the subject comprise oxygen saturation and respiratory airflow, and wherein classifying a severity level of a respiratory event comprises:
classifying a severity level of a decrease in oxygen saturation associated with the respiratory event into one of n categories;
classifying a severity level of a decrease in respiratory airflow associated with the respiratory event into one of m categories; and
determining the magnitude of severity of the respiratory event using an nxm matrix based on the severity levels of the decrease in oxygen saturation and the decrease in respiratory airflow associated with the respiratory event, where n and m are integers>1, and wherein adjusting a protrusion level of the adjustable mandibular displacement device during the test period comprises determining at least one of a magnitude and rate of adjustment of the protrusion level based on the magnitude of the severity determined using the nxm matrix.

19. The system of claim 18, wherein m is 3, and a first category corresponds to an approximately 80-100% decrease in respiratory airflow, a second category corresponds to an approximately 45-79% decrease in respiratory airflow, and a third category corresponds to an approximately 30-44% decrease in respiratory airflow.

20. The system of claim 18, wherein n is 3, and a first category corresponds to at least an approximately 6% decrease in oxygen saturation from real-time or baseline oxygen saturation, a second category corresponds to between an approximately 3% and 6% decrease in oxygen saturation from real-time or baseline oxygen saturation and a third category corresponds to a less than an approximately 3% decrease in oxygen saturation from real-time or baseline oxygen saturation.

21. The system of claim 18, wherein the memory has further computer-executable instructions stored thereon that, when executed by the processing unit, cause the system to:
calculate a frequency of the respiratory event; and
multiply the frequency of the respiratory event by the magnitude of severity of the respiratory event using an nxm matrix to obtain a frequency-severity index, wherein adjusting a protrusion level of the adjustable mandibular displacement device during the test period comprises determining at least one of the magnitude and rate of adjustment of the protrusion level based on the frequency-severity index.

22. The system of claim 17, wherein the memory has further computer-executable instructions stored thereon that, when executed by the processing unit, cause the system to classify a frequency level of the respiratory event into one of q categories and obtain a frequency-severity index using an nxmxq matrix based on the severity and frequency levels associated with the respiratory event, where n and m and q are integers>1, and wherein adjusting a protrusion level of the adjustable mandibular displacement device during the test period comprises determining at least one of a magnitude and rate of adjustment of the protrusion level based on the frequency-severity index.

23. The system of claim 1, wherein detecting one or more respiratory events comprises detecting a decrease in oxygen saturation within a period of time after detecting a decrease in respiratory airflow.

24. The system of claim 23, wherein the period of time is subject-specific and determined based on an analysis of the detected respiratory events.

25. The system of claim 24, wherein the analysis is performed before or during the test period.

26. The system of claim 23, wherein the period of time is fixed and approximately 10-40 seconds.

27. The system of claim 1, wherein the monitoring unit comprises an air flow monitor, and the physiological information from the subject during the test period further comprises respiratory airflow.

28. The system of claim 1, wherein adjusting a protrusion level of the adjustable mandibular displacement device during the test period is performed automatically.

29. The system of claim 1, wherein monitoring unit further comprises an airflow monitor and an oxygen saturation monitor, and the one or more physiological inputs from the subject comprise oxygen saturation and respiratory airflow, or wherein the monitoring unit further comprises an airflow monitor and a sound monitor or a vibration monitor, and the one or more physiological inputs from the subject comprise respiratory airflow and acoustic energy or vibration generated by the subject, or wherein the monitoring unit further comprises a polysomnograph, and the one or more physiological inputs further comprise at least one of sleep stage, sleep position and force applied on the subject's teeth by the adjustable mandibular displacement device.

30. The system of claim 1, wherein the test period is while the subject is sleeping.

31. The system of claim 1, wherein the test period is a single sleep session or the test period includes multiple sleep sessions.

32. The system of claim 1, wherein adjusting a protrusion level of the adjustable mandibular displacement device during the test period comprises at least one of increasing protrusion level or decreasing protrusion level of the adjustable mandibular displacement device.

33. The system of claim 1, wherein a greater magnitude or rate of adjustment of the protrusion level of the adjustable mandibular displacement device corresponds to a more frequent or severe respiratory event, and a lesser magnitude or rate of adjustment of the protrusion level of the adjustable mandibular displacement device corresponds to a less frequent or severe respiratory event.

34. The system of claim 1, wherein the test period has a duration less than one night.

35. The system of claim 1, wherein the memory has further computer-executable instructions stored thereon that, when executed by the processing unit, cause the system to:
classify a frequency level of at least one of the one or more respiratory events, and wherein adjusting a protrusion level of the adjustable mandibular displacement device during the test period comprises determining at least one of a magnitude and rate of adjustment of the protrusion level based on the frequency level of the respiratory event.

36. The system of claim 1, wherein adjusting a protrusion level of the adjustable mandibular displacement device during the test period comprises at least one of:
in response to not detecting a respiratory event during a fixed period of time during the test period, adjusting protrusion level to induce a change in respiratory airflow, or
in response to a frequency of respiratory events falling below a predetermined threshold, adjusting protrusion level of the adjustable mandibular displacement device to optimize respiratory airflow.

37. The system of claim 1, wherein the one or more respiratory events are at least one of an apnea, a hypopnea, a flow limited breath or a snoring event.

38. A system for performing a titration for oral appliance therapy based on data collected at a plurality of protrusion levels, comprising:
an adjustable mandibular displacement device configured to be positioned in an oral cavity of a subject; and
a control unit comprising a processing unit and a memory operatively coupled to the processing unit, the memory having computer-executable instructions stored thereon that, when executed by the processing unit, cause the system to:
receive physiological data collected from a subject during a test period;
detect one or more respiratory events using the physiological data;
receive data related to a protrusion level of the adjustable mandibular displacement device during the test period;
adjust the protrusion level of the adjustable mandibular displacement device during the test period based on at least one of frequency or severity of the one or more respiratory events, at least one of a magnitude or rate of adjustment being related to at least one of the frequency or the severity of the one or more respiratory events; and
evaluate an outcome of oral appliance therapy with a mandibular repositioning appliance based on the physiological data collected from the subject at the plurality of protrusion levels of the adjustable mandibular displacement device during the test period.

39. The system of claim 38, wherein evaluating an outcome of oral appliance therapy further comprises comparing a frequency of occurrence of the one or more respiratory events at different protrusion levels.

40. The system of claim 39, wherein the memory has further computer-executable instructions stored thereon that, when executed by the processing unit, cause the system to determine that the subject is a candidate for oral appliance therapy if the frequency occurrence of the one or more respiratory events decreases between successively greater protrusion levels.

41. The system of claim 38, wherein the data related to the protrusion level of the adjustable mandibular displacement device comprises an amount of time the adjustable mandibular displacement device spends at each of the plurality of protrusion levels.

42. The system of claim 38, wherein the evaluation comprises predicting an effective protrusion level of the adjustable mandibular displacement device.

43. A method for performing a titration for oral appliance therapy, comprising:
positioning an adjustable mandibular displacement device in an oral cavity of a subject during a test period;
monitoring physiological information from the subject during the test period;
detecting one or more respiratory events during the test period using the physiological information;
adjusting a protrusion level of the adjustable mandibular displacement device during the test period based on at least one of frequency or severity of the one or more respiratory events, at least one of a magnitude or rate of adjustment being related to at least one of the frequency or the severity of the one or more respiratory events; and
evaluating the outcome of oral appliance therapy with a mandibular repositioning appliance based on a history of movement of the adjustable mandibular displacement device and the physiological information during the test period.

44. A method for performing a titration for oral appliance therapy based on data collected at a plurality of protrusion levels of an adjustable mandibular displacement device, comprising:
receiving physiological data collected from a subject during a test period;
detecting one or more respiratory events during the test period using the physiological data;
receiving data related to a protrusion level of the adjustable mandibular displacement device during the test period;
adjusting the protrusion level of the adjustable mandibular displacement device during the test period based on at least one of frequency or severity of the one or more respiratory events, at least one of a magnitude or rate of adjustment being related to at least one of the frequency or the severity of the one or more respiratory events; and
evaluating an outcome of oral appliance therapy with a mandibular repositioning appliance based on the physiological data collected from the subject at the plurality of protrusion levels of the adjustable mandibular displacement device during the test period.

* * * * *

UNITED STATES PATENT AND TRADEMARK OFFICE
CERTIFICATE OF CORRECTION

PATENT NO. : 10,172,548 B2
APPLICATION NO. : 14/774949
DATED : January 8, 2019
INVENTOR(S) : John Remmers et al.

Page 1 of 1

It is certified that error appears in the above-identified patent and that said Letters Patent is hereby corrected as shown below:

In the Claims

Column 49, Line 44 Claim 1, "period using the one or more psychological inputs;" should read --period using the one or more physiological inputs;--

Signed and Sealed this
Sixteenth Day of July, 2019

Andrei Iancu
*Director of the United States Patent and Trademark Office*